(12) United States Patent
Medoff et al.

(10) Patent No.: US 9,777,430 B2
(45) Date of Patent: *Oct. 3, 2017

(54) RECONFIGURABLE PROCESSING ENCLOSURES

(71) Applicant: Xyleco, Inc., Wakefield, MA (US)

(72) Inventors: Marshall Medoff, Brookline, MA (US); Thomas Craig Masterman, Rockport, MA (US); Robert Paradis, Burlington, MA (US)

(73) Assignee: XYLECO, INC., Wakefield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/178,166

(22) Filed: Jun. 9, 2016

(65) Prior Publication Data

US 2017/0036185 A1 Feb. 9, 2017

Related U.S. Application Data

(63) Continuation of application No. 14/299,005, filed on Jun. 9, 2014, now Pat. No. 9,388,442, which is a
(Continued)

(51) Int. Cl.
*B01J 19/08* (2006.01)
*C12M 1/00* (2006.01)
(Continued)

(52) U.S. Cl.
CPC ............. *D21C 9/007* (2013.01); *B01D 15/02* (2013.01); *B01D 53/32* (2013.01); *B01D 61/44* (2013.01);
(Continued)

(58) Field of Classification Search
CPC .............. B01J 19/085; B01J 2219/0879; B01J 2219/0869; C10G 1/00; C12M 47/10;
(Continued)

(56) References Cited

U.S. PATENT DOCUMENTS 2,674,381 A   4/1954   Cady
2,993,120 A   7/1961   Emannelson
(Continued)

FOREIGN PATENT DOCUMENTS

CN   202670653 U   1/2013
EP   0458162 A1   11/1991
(Continued)

OTHER PUBLICATIONS

International Search Report and Written Opinion issued in International Application No. PCT/US2014/021629, dated Jul. 11, 2014 (6 pages).
(Continued)

*Primary Examiner* — Nicole Ippolito
(74) *Attorney, Agent, or Firm* — Leber IP Law

(57) ABSTRACT

Biomass (e.g., plant biomass, animal biomass, and municipal waste biomass) or other materials are processed to produce useful intermediates and products, such as energy, fuels, foods or materials. For example, systems and methods are described that can be used to treat feedstock materials, such as cellulosic and/or lignocellulosic materials, in a vault in which the walls and optionally the ceiling include discrete units. Such vaults are re-configurable.

26 Claims, 8 Drawing Sheets

Related U.S. Application Data continuation of application No. PCT/US2014/021629, filed on Mar. 7, 2014.

(60) Provisional application No. 61/793,336, filed on Mar. 15, 2013, provisional application No. 61/774,773, filed on Mar. 8, 2013, provisional application No. 61/774,731, filed on Mar. 8, 2013, provisional application No. 61/774,723, filed on Mar. 8, 2013, provisional application No. 61/774,780, filed on Mar. 8, 2013, provisional application No. 61/774,775, filed on Mar. 8, 2013, provisional application No. 61/774,684, filed on Mar. 8, 2013, provisional application No. 61/774,735, filed on Mar. 8, 2013, provisional application No. 61/774,740, filed on Mar. 8, 2013, provisional application No. 61/774,744, filed on Mar. 8, 2013, provisional application No. 61/774,746, filed on Mar. 8, 2013, provisional application No. 61/774,750, filed on Mar. 8, 2013, provisional application No. 61/774,752, filed on Mar. 8, 2013, provisional application No. 61/774,754, filed on Mar. 8, 2013, provisional application No. 61/774,761, filed on Mar. 8, 2013.

(51) Int. Cl.

| | | |
|---|---|---|
| C13K 13/00 | (2006.01) | |
| C12P 19/02 | (2006.01) | |
| C12P 19/14 | (2006.01) | |
| C13K 1/02 | (2006.01) | |
| C10G 1/00 | (2006.01) | |
| C12P 7/10 | (2006.01) | |
| D21C 9/00 | (2006.01) | |
| B01D 53/32 | (2006.01) | |
| B01D 15/02 | (2006.01) | |
| E04B 1/92 | (2006.01) | |
| G21F 7/00 | (2006.01) | |
| H01J 37/317 | (2006.01) | |
| B65G 53/40 | (2006.01) | |
| C12P 7/06 | (2006.01) | |
| B01D 61/44 | (2006.01) | |
| C12P 7/52 | (2006.01) | |
| C10L 9/08 | (2006.01) | |
| C07C 29/149 | (2006.01) | |
| B65G 27/00 | (2006.01) | |
| B65G 53/04 | (2006.01) | |

(52) U.S. Cl.
CPC ............ *B01J 19/085* (2013.01); *B65G 27/00* (2013.01); *B65G 53/04* (2013.01); *B65G 53/40* (2013.01); *C07C 29/149* (2013.01); *C10G 1/00* (2013.01); *C10L 9/08* (2013.01); *C12M 47/00* (2013.01); *C12M 47/10* (2013.01); *C12P 7/06* (2013.01); *C12P 7/10* (2013.01); *C12P 7/52* (2013.01); *C12P 19/02* (2013.01); *C12P 19/14* (2013.01); *C13K 1/02* (2013.01); *C13K 13/002* (2013.01); *E04B 1/92* (2013.01); *G21F 7/00* (2013.01); *H01J 37/317* (2013.01); *B01J 2219/0869* (2013.01); *B01J 2219/0879* (2013.01); *B01J 2219/0886* (2013.01); *C12P 2203/00* (2013.01); *E04B 2001/925* (2013.01); *H01J 2237/202* (2013.01); *H01J 2237/31* (2013.01); *H01J 2237/3165* (2013.01); *Y02E 50/16* (2013.01); *Y02E 50/17* (2013.01); *Y02E 50/32* (2013.01); *Y02E 50/343* (2013.01); *Y02E 60/17* (2013.01); *Y02P 20/136* (2015.11); *Y02W 10/33* (2015.05); *Y02W 10/37* (2015.05)

(58) Field of Classification Search
CPC .. C12P 7/10; C12P 19/02; C12P 19/14; C12P 2203/00; C13K 1/02; C13K 13/002
USPC .... 250/453.11, 454.11, 455.11, 492.1, 492.3
See application file for complete search history.

(56) References Cited

U.S. PATENT DOCUMENTS

| | | |
|---|---|---|
| 3,844,890 A | 10/1974 | Horikoshi et al. |
| 3,934,144 A | 1/1976 | Green et al. |
| 3,939,286 A | 2/1976 | Jelks |
| 4,243,750 A | 1/1981 | Muller et al. |
| 4,261,905 A | 4/1981 | Preobrazhenskaya et al. |
| 4,268,505 A | 5/1981 | Yoshikumi et al. |
| 4,274,163 A | 6/1981 | Malcom et al. |
| 4,275,163 A | 6/1981 | Gallo |
| 4,303,649 A | 12/1981 | Jones |
| 4,305,000 A | 12/1981 | Cheever |
| 4,321,328 A | 3/1982 | Hoge |
| 4,337,152 A | 6/1982 | Lynch |
| 4,387,476 A | 6/1983 | Bueb et al. |
| 4,435,307 A | 3/1984 | Barbesgaard et al. |
| 4,482,046 A | 11/1984 | Kraus |
| 4,760,264 A | 7/1988 | Barrett |
| 4,769,082 A | 9/1988 | Kumakura et al. |
| 4,813,532 A | 3/1989 | Harper |
| 5,055,204 A | 10/1991 | Bogart |
| RE33,935 E | 5/1992 | Fujimoto et al. |
| 5,122,598 A | 6/1992 | della Valle et al. |
| 5,131,525 A | 7/1992 | Musschoot |
| 5,181,715 A | 1/1993 | Ohkoda et al. |
| 5,314,978 A | 5/1994 | Kim et al. |
| 5,392,529 A | 2/1995 | Bailey et al. |
| 5,396,074 A | 3/1995 | Peck et al. |
| 5,401,973 A | 3/1995 | McKeown et al. |
| 5,462,155 A | 10/1995 | Demar et al. |
| 5,530,255 A | 6/1996 | Lyons et al. |
| 5,538,730 A | 7/1996 | Romeo et al. |
| 5,593,890 A | 1/1997 | Flores-Cotera et al. |
| 5,621,270 A | 4/1997 | Allen |
| 5,635,714 A | 6/1997 | Nablo et al. |
| 5,661,305 A | 8/1997 | Lawrence et al. |
| 5,753,474 A | 5/1998 | Ramey |
| 5,876,505 A | 3/1999 | Klyosov et al. |
| 5,877,582 A | 3/1999 | Nishimura |
| 5,882,737 A | 3/1999 | Eckhoff |
| 5,916,780 A | 6/1999 | Foody et al. |
| 5,916,929 A | 6/1999 | Knobel et al. |
| 5,994,706 A | 11/1999 | Allen et al. |
| 6,011,008 A | 1/2000 | Domb et al. |
| 6,127,687 A | 10/2000 | Williams et al. |
| 6,220,427 B1 | 4/2001 | Ratz et al. |
| 6,528,800 B1 | 3/2003 | Dzwierzynski et al. |
| 6,555,350 B2 | 4/2003 | Ahring et al. |
| 6,608,882 B2 | 8/2003 | Allen et al. |
| 6,620,605 B2 | 9/2003 | Fowler et al. |
| 6,628,750 B1 | 9/2003 | Korenev |
| 6,707,049 B1 | 3/2004 | Lyons et al. |
| 6,713,773 B1 | 3/2004 | Lyons et al. |
| 6,780,448 B1 | 8/2004 | Howard |
| 6,808,600 B2 | 10/2004 | Ross et al. |
| 6,833,551 B2 | 12/2004 | Avnery |
| 6,838,678 B1 | 1/2005 | Bujak et al. |
| 7,019,155 B2 | 3/2006 | Manzer |
| 7,025,874 B2 | 4/2006 | Chan et al. |
| 7,153,533 B2 | 12/2006 | Burke et al. |
| 7,402,428 B2 | 7/2008 | Forster et al. |
| 7,408,056 B2 | 8/2008 | Medoff et al. |
| 7,846,295 B1 | 12/2010 | Medoff |
| 7,867,358 B2 | 1/2011 | Medoff |
| 7,867,359 B2 | 1/2011 | Medoff |
| 7,900,857 B2 | 3/2011 | Medoff |
| 7,931,784 B2 | 4/2011 | Medoff |
| 7,932,065 B2 | 4/2011 | Medoff |
| 7,935,219 B2 | 5/2011 | Medoff |
| 7,971,809 B2 | 7/2011 | Medoff |

(56) References Cited

U.S. PATENT DOCUMENTS

| | | | |
|---|---|---|---|
| 8,052,838 B2 | 11/2011 | Medoff | |
| 8,070,912 B2 | 12/2011 | Medoff | |
| 8,074,910 B2 | 12/2011 | Medoff | |
| 8,083,906 B2 | 12/2011 | Medoff | |
| 8,142,620 B2 | 3/2012 | Medoff | |
| 8,147,655 B2 | 4/2012 | Medoff | |
| 8,168,038 B2 | 5/2012 | Medoff | |
| 8,212,087 B2 | 7/2012 | Medoff | |
| 8,221,585 B2 | 7/2012 | Medoff | |
| 8,236,535 B2 | 8/2012 | Medoff et al. | |
| 8,318,453 B2 | 11/2012 | Medoff | |
| 8,415,122 B2 | 4/2013 | Medoff et al. | |
| 8,597,472 B2 | 12/2013 | Medoff | |
| 8,911,833 B2 | 12/2014 | Medoff | |
| 8,951,778 B2 | 2/2015 | Medoff et al. | |
| 9,334,518 B2 * | 5/2016 | Medoff | B01J 19/085 |
| 9,388,442 B2 * | 7/2016 | Medoff | B01J 19/085 |
| 9,464,334 B2 * | 10/2016 | Medoff | B01J 19/085 |
| 9,499,939 B2 * | 11/2016 | Medoff | C13K 1/02 |
| 2002/0182294 A1 | 12/2002 | Allen et al. | |
| 2003/0094578 A1 | 5/2003 | Nelson | |
| 2003/0094581 A1 | 5/2003 | Rose | |
| 2003/0217383 A1 | 11/2003 | Reuber et al. | |
| 2003/0218414 A1 | 11/2003 | Avnery | |
| 2004/0005674 A1 | 1/2004 | Duck et al. | |
| 2004/0065589 A1 | 4/2004 | Jorgensen | |
| 2004/0113094 A1 | 6/2004 | Lyons et al. | |
| 2004/0173533 A1 | 9/2004 | Farone et al. | |
| 2004/0183032 A1 | 9/2004 | Fink et al. | |
| 2006/0088922 A1 | 4/2006 | Yang et al. | |
| 2006/0196622 A1 | 9/2006 | Trung et al. | |
| 2006/0251764 A1 | 11/2006 | Abbas et al. | |
| 2007/0015855 A1 | 1/2007 | Medoff et al. | |
| 2007/0037259 A1 | 2/2007 | Hennessey et al. | |
| 2007/0040130 A1 | 2/2007 | Nanataki et al. | |
| 2007/0077630 A1 | 4/2007 | Harris et al. | |
| 2007/0134781 A1 | 6/2007 | Agblevor | |
| 2007/0200262 A1 | 8/2007 | Hills | |
| 2007/0215821 A1 | 9/2007 | Stirling et al. | |
| 2008/0248540 A1 | 10/2008 | Yang | |
| 2008/0313954 A1 | 12/2008 | Lee et al. | |
| 2009/0031026 A1 | 1/2009 | Tanner et al. | |
| 2009/0067575 A1 | 3/2009 | Seppi et al. | |
| 2009/0090654 A1 | 4/2009 | Duyvesteyn et al. | |
| 2009/0120256 A1 | 5/2009 | Pasek | |
| 2009/0181433 A1 | 7/2009 | Chotani et al. | |
| 2009/0203079 A1 | 8/2009 | Sticklen et al. | |
| 2009/0286295 A1 | 11/2009 | Medoff et al. | |
| 2010/0064746 A1 | 3/2010 | Medoff | |
| 2010/0087687 A1 | 4/2010 | Medoff | |
| 2010/0093241 A1 | 4/2010 | Medoff | |
| 2010/0105119 A1 | 4/2010 | Medoff | |
| 2010/0108567 A1 | 5/2010 | Medoff | |
| 2010/0112242 A1 | 5/2010 | Medoff | |
| 2010/0124583 A1 | 5/2010 | Medoff | |
| 2010/0124772 A1 | 5/2010 | Sabesan | |
| 2010/0146870 A1 | 6/2010 | Zeik et al. | |
| 2010/0159569 A1 | 6/2010 | Medoff et al. | |
| 2010/0179315 A1 | 7/2010 | Medoff | |
| 2010/0200806 A1 | 8/2010 | Medoff et al. | |
| 2010/0203495 A1 | 8/2010 | Medoff et al. | |
| 2010/0206501 A1 | 8/2010 | Medoff | |
| 2010/0229256 A1 | 9/2010 | Somleva et al. | |
| 2010/0297705 A1 | 11/2010 | Medoff et al. | |
| 2010/0297720 A1 | 11/2010 | Medoff et al. | |
| 2011/0011960 A1 | 1/2011 | Medoff | |
| 2011/0027837 A1 | 2/2011 | Medoff | |
| 2011/0039317 A1 | 2/2011 | Medoff | |
| 2011/0081335 A1 | 4/2011 | Medoff | |
| 2011/0081336 A1 | 4/2011 | Medoff | |
| 2011/0107659 A1 | 5/2011 | Gruter et al. | |
| 2011/0111456 A1 | 5/2011 | Medoff | |
| 2011/0139383 A1 | 6/2011 | Medoff | |
| 2011/0155559 A1 | 6/2011 | Medoff | |
| 2011/0192989 A1 | 8/2011 | Yaniv et al. | |
| 2011/0262985 A1 | 10/2011 | Medoff | |
| 2011/0265991 A1 | 11/2011 | Medoff | |
| 2011/0287498 A1 | 11/2011 | Medoff et al. | |
| 2012/0003704 A1 | 1/2012 | Medoff | |
| 2012/0052536 A1 | 3/2012 | Medoff et al. | |
| 2012/0074337 A1 | 3/2012 | Medoff | |
| 2012/0077247 A1 | 3/2012 | Medoff | |
| 2012/0094355 A1 | 4/2012 | Medoff | |
| 2012/0094358 A1 | 4/2012 | Medoff | |
| 2012/0100577 A1 | 4/2012 | Medoff et al. | |
| 2012/0100586 A1 | 4/2012 | Medoff et al. | |
| 2012/0142065 A1 | 6/2012 | Medoff | |
| 2012/0142068 A1 | 6/2012 | Medoff | |
| 2012/0237984 A1 | 9/2012 | Medoff | |
| 2012/0309060 A1 | 12/2012 | Medoff | |
| 2012/0315675 A1 | 12/2012 | Medoff et al. | |
| 2012/0316376 A1 | 12/2012 | Medoff | |
| 2012/0322117 A1 | 12/2012 | Anton et al. | |
| 2013/0052682 A1 | 2/2013 | Medoff et al. | |
| 2013/0052687 A1 | 2/2013 | Medoff et al. | |
| 2013/0158302 A1 | 6/2013 | Duff et al. | |
| 2014/0011248 A1 | 1/2014 | Medoff et al. | |

FOREIGN PATENT DOCUMENTS

| | | |
|---|---|---|
| EP | 2008668 A | 12/2008 |
| EP | 2276795 A2 | 1/2011 |
| GB | 721235 A | 1/1955 |
| JP | 6-333699 | 12/1994 |
| JP | 11-337700 A | 12/1999 |
| JP | 2003111356 A | 4/2003 |
| JP | 2008161137 A | 7/2008 |
| JP | 2010041923 A | 2/2010 |
| JP | 2011024545 A | 2/2011 |
| RU | 2432400 C2 | 10/2011 |
| WO | WO-2006032282 A1 | 3/2006 |
| WO | WO-2006102543 A2 | 9/2006 |
| WO | WO-2007/054610 A1 | 5/2007 |
| WO | WO-2008011598 A2 | 1/2008 |
| WO | WO-2008073186 A2 | 6/2008 |
| WO | WO-2009134791 A2 | 11/2009 |
| WO | WO-2009155601 A2 | 12/2009 |
| WO | WO-2010135380 A1 | 11/2010 |
| WO | WO-2011/063500 A1 | 6/2011 |
| WO | WO-2011133536 A1 | 10/2011 |
| WO | WO-2012006438 | 1/2012 |
| WO | WO-2013096693 A1 | 6/2013 |
| WO | WO-2013096700 A1 | 6/2013 |
| WO | WO-2013101977 A1 | 7/2013 |
| WO | WO-2014059113 A1 | 4/2014 |
| WO | WO-2014059140 A1 | 4/2014 |

OTHER PUBLICATIONS

International Search Report and Written Opinion issued by the U.S. Patent and Trademark Office as International Searching Authority for International Application No. PCT/US2014/021796 dated May 21, 2014 (7 pages).

Alfernore, S., et al. "Improving ethanol production and viability of *Saccharomyces cerevisiae* by a vitamin feeding strategy during fed-batch process," Applied Microbiology and Biotechnology, vol. 60, No. 1, pp. 67-72 (Oct. 2002).

Awafo, V. A., et al., "Effect of Irradiation, as a Pretreatment, on Bioconversion of Corn Stover into Protein-rich Mycelial Biomass of Pluerotus Sajor-Caju," Radiation Physics and Chemistry, vol. 46, No. 4-6, pp. 1299-1302 (Sep. 12, 1995).

Bak, J. S., et al., "Improved enzymatic hydrolysis yield of rice straw using electron beam irradiation pretreatment," Bioresource Technology, vol. 100, No. 3, pp. 1285-1290 (Feb. 2009).

Baucher, M., et al., "Lignin: Genetic Engineering and Impact on Pulping," Critical Review in Biochemistry and Molecular Biology, vol. 38, No. 4, pp. 305-350 (Jan. 1, 2003).

Chen, F. and Dixon, R. A., "Lignin Modification Improves Fermentable Sugar Yields for Biofuel Production," Nature Biotechnology, vol. 25, No. 7, pp. 759-761 (Jul. 2007).

(56) References Cited

OTHER PUBLICATIONS

Chu, William T., "Overview of Light-Ion Beam Therapy," Columbus-Ohio, ICRU-IAEA Meeting, pp. 1-20 (Mar. 18-20, 2006).
Chunping, Y., et al., "Effect and aftereffect of gamma radiation pretreatment on enzymatic hydrolysis of wheat straw," Bioresource Technology, vol. 99, No. 14, pp. 6240-6245 (Sep. 2008).
De Kerf, M., et al., "Characterization and Disintegration Properties of Irradiated Starch," International Journal of Pharmaceutics, vol. 221, No. 1-2, pp. 69-76 (Jun. 19, 2001).
Eichenberger, C., et al., "7.5 MeV High Average Power Linear Accelerator System for Food Irradiation Applications," Proceedings of the International Symposium on the New Frontier of Irradiated Food and Non-Food Products at King Mongkut's University of Technology Thonburi (KMUTT), 8 pages (Sep. 2005).
Ghosh, P. and Singh, A., "Physicochemical and Biological Treatments for Enzymatic/Microbial Conversion of Lignocellulosic Biomass," Advances in Applied Microbiology, vol. 39, pp. 295-333 (1993).
Graham-Rowe, Duncan, "Electron Beams Could be Used to Irradiate Post," Daily News, 2 pages (Oct. 24, 2001).
Gromov, A. V., "VI Inter-University Conference on Electron Accelerators," Atomic Energy, vol. 21, No. 2, pp. 143-145 (Aug. 1966).
Han, Y. W., et al., "Chemical and Physical Properties of Sugarcane Bagasse Irradiated with Gamma Rays," J. Agric. Food Chem., vol. 31, No. 1, pp. 34-38 (1983).
Han, Y. W., et al., "Effect of Gamma-Ray Irradiation on Alcohol Production From Corn," Biotechnol. Bioeng., vol. 25, No. 11, pp. 2631-2640 (Nov. 1983).
Hanis, T., et al., "Effect of Gamma Irradiation on Survival of Natural Microflora and Some Nutrients in Cereal Meals," Cereal Chemistry, vol. 65, No. 5, pp. 381-383 (1988).
Ibrahim, M. N. M. and Pearce, G. R., "Effects of Gamma Radiation on the Composition and In Vitro Digestibility of Crop By-products," Agricultural Wastes, vol. 2, pp. 253-259 (Oct.-Dec. 1980).
International Search Report and Written Opinion issued by the European Patent Office as International Searching Authority for International Application No. PCT/US2012/024970 dated Sep. 14, 2012 (19 pages).
International Search Report and Written Opinion issued by the European Patent Office as International Searching Authority for International Application No. PCT/US2012/025023 dated Apr. 25, 2012 (11 pages).
International Search Report and Written Opinion issued by the U.S. Patent and Trademark Office as International Searching Authority for International Application No. PCT/US2013/064332 dated Feb. 14, 2014 (11 pages).
Iwata, Y., et al., "Alternating-Phase-Focused IH-DTL for Heavy-Ion Medical Accelerators," Proceedings of EPAC 2006, WEPCH169, 08 Applications of Accelerators, Technology Transfer and Industrial Relations, U01 Medical Applications, Edinburgh, Scotland, pp. 2328-2330 (2006).
Kang, L., et al., "Bioconversion of kraft paper mill sludges to ethanol by SSF and SSCF," Appl. Biochem. Biotechnol., vol. 161, No. 1-8, pp. 53-66 (May 2010).
Khan, A. W., et al., "Effect of Electron-Beam Irradiation Pretreatment on the Enzymatic Hydrolysis of Softwood," Biotechnol. Bioeng., vol. 28, pp. 1449-1453 (Sep. 1986).
Krane, Kennth S., "Introductory Nuclear Physics," John Wiley & Sons, Inc., 858 pages. (1988).
Kamakura, M. and Kaetsu, I., "Radiation Degradation and the Subsequent Enzymatic Hydrolysis of Waste Papers," Biotechnol. Bioeng., vol. 24, pp. 991-997 (Apr. 1982).
Kumar, P., et al., "Methods for Pretreatment of Lignocellulosic Biomass for Efficient Hydrolysis and Biofuel Production," Ind. Eng. Chem. Res., vol. 48, No. 8, pp. 3713-3729 (Jan. 1, 2009).
Leitner, M. A., et al., "Status of the Superconducting ECR Ion Source Venus," Proceedings of the EPAC 2000, Vienna, Austria, 3 pages (2000).
Leonhardt, J. W., et al., "Gamma and Electron Radiation Effects on Straw," Radial. Phys. Chem., vol. 21, No. 4, pp. 397-400 (1983).
Levy, I., et al., "Modification of polysaccharides and plant cell wall by endo-1 ,4,beta-glucanase and cellulose- binding domains," Biomolecular Engineering, vol. 19, No. 1, pp. 17-30 (Jun. 2002).
Miyamoto, Kazuhisa, "Chapter 3.2 Cellulase Production," Renewable Biological Systems for Alternative Sustainable Energy Production, FAO Agricultural Services Bulletin, #128, 13 pages (1997).
Philippidis, G. P., "Cellulose bioconversion technology," Chapter 12 in Handbook on Bioethanol: Production and Utilization, Taylor & Francis, Washington, D.C., pp. 179-212, 35 pages. (1996).
Prelec, Krsto, "Ions and Ion Accelerators for Cancer Treatment," FIZIKA B, vol. 6, No. 4, pp. 177-206 (1997).
Saleh, F., et al., "Carbohydrases are Digested by Proteases Present in Enzyme Preparations During in vitro Digestion," J. Poultry Sci., vol. 41, pp. 229-235 (2004).
Sarath, G., et al., "Opportunities and roadblocks in utilizing forages and small grains for liquid fuels," J. Ind. Microbiol. Biotechnol., vol. 35, pp. 343-354 (2008).
Scharf, W. and Wieszczycka, W., "Electron Accelerators for Industrial Processing—a Review", 15th International Conference on the Applications of Accelerators in Research and Industry, Denton, TX, USA, pp. 949-952 (1999).
Seiboth, B., et al., "Chapter 13: Trichoderma reesei: A Fungal Enzyme Producer for Cellulosic Biofuels," Biofuel Production— Recent Developments and Prospects, pp. 309-340, 33 pages. (2011).
Smith, G. S., et al., "Irradiation Enhancement of Biomass Conversion," Radiation Physics and Chemistry, vol. 25, Nos. 1-3, pp. 27-33 (Jan. 1, 1985).
Stevens, Robert W., "On the Stowage of Ships and Their Cargoes," Section 190 Fermentation, Nabu Press, 3 pages (Jan. 7, 2010).
Taherzadeh, M. J. and Karimi, K., "Pretreatment of Lignocellulosic Wastes to Improve Ethanol and Biogas Production: A Review," Int. J. Mol. Sci., vol. 9, pp. 1621-1651 (2008).
Tewari, H. K., et al., "Role of Pretreatments on Enzymatic Hydrolysis of Agricultural Residues for Reducing Sugar Production," J. Chem. Tech. Biotechnol., vol. 38, No. 3, pp. 153-165 (1987).
Wang, J. S., et al., "Efficient Cellulase Production from Corn Straw by Trichoderma Reesei LW1 Through Solid State Fermentation Process," Ethnobotanical Leaflets, vol. 2005, No. 1, Article 7, 8 pages (2005).
Wayman, M., et al., "Bioconversion of Waste Paper to Ethanol," Process Biochemistry, vol. 27, No. 4, pp. 239-245 (Jul. 1992).
Whitham, K., et al., "12 MW, 100 KW, 7000 Hour/Year Modulator for Titan Scan," Tenth IEEE International Pulsed Power Conference, Digest of Technical Papers, vol. 1, pp. 534-538 (Jul. 3-6, 1995).
Wilson, Ian, "Filler and Coating Pigments for Papermakers," Industrial Minerals and Rocks: Commodities, Markets and Uses, Part III, No. 96, pp. 1287-1300 (2006).
Xia, L., et al., "Saccharification of Corn Stover by Immobilized Trichoderma reesei cells," Wei Shen Wu Xue Bao, vol. 38, No. 2, pp. 114-119 (Apr. 1998).
Yamanda, N., et al., "Decomposition Behavior of Waste Paper with Hot Compressed Water," Journal of the Japan Institute of Energy, vol. 79, No. 6, pp. 540-547 (Jun. 2000).
Eriez Magnetics, "How to Choose and Use Vibratory Feeders and Conveyors," 16 pages (2007).
Machine Translation of JP11337700 Mutsumi et al. pp. 1-4 1999.
Korolev,S., et al., "Characteristics of Sealed-Off Electron Gun with wide Beam," Proceedings of EPAC 2004, Lucerne, Switzerland, pp. 2727-2729 (2004).
McMillan, Gregory J., "Analysis of Vibratory Equipment Using the Finite Element Method," A Research Paper Submitted in Partial Fulfillment of the Requirements for the Master of Science Degree in Manufacturing Engineering; The Graduate School University of Wisconsin-Stout, 59 pages (May 2011).
International Search Report and Written Opinion issued by the U.S. Patent and Trademark Office as International Searching Authority for International Application No. PCT/US2013/064320 dated May 20, 2014 (14 pages).
International Search Report and Written Opinion issued by the U.S. Patent and Trademark Office as International Searching Authority for International Application No. PCT/US2013/064317 dated Mar. 7, 2014 (9 pages).

(56) References Cited

OTHER PUBLICATIONS

International Search Report and Written Opinion issued by the European Patent Office as International Search Authority for International Application No. PCT/US2010/023957 dated Jan. 3, 2011 (17 pages).

Khan, A. W., et al., "Electron beam irradiation pretreatment and enzymatic saccharification of used newsprint and paper mill wastes," International Journal of Radiation Applications and Instrumentation. Part C. Radiation Physics and Chemistry, vol. 29, Issue 2, pp. 117-120 (1987).

Wooley, R., et al., "A Nine-Zone Simulating Moving Bed for the Recovery of Glucose and Xylose from Biomass Hydrolyzate," Ind. Eng. Chem. Res., vol. 37, pp. 3699-3709 (1998).

Carter, B., et al., "Removal and Recovery of Furfural, 5-Hydroxymethylfurfural, and Acetic Acid From Aqueous Solutions Using a Soluble Polyelectrolyte," Biotechnology and Bioengineering, vol. 108, No. 9, pp. 2046-2052 (Mar. 14, 2011).

Sluiter, J. B., et al., "Compositional Analysis of Lignocellulosic Feedstocks. 1. Review and Description of Methods," Journal of Agricultural and Food Chemistry, vol. 58, pp. 9043-9053 (2010).

Palmqvist, E. and Hahn-Hagerdal, B., "Fermentation of lignocellulosic hydrolysates. II: inhibitors and mechanisms of inhibition," Bioresource Technology, vol. 74, pp. 25-33 (2000).

Tao, F., et al., "Efficient process for the conversion of xylose to furfural with acidic ionic liquid," Can. J. Chem, vol. 89, pp. 83-87 (Dec. 13, 2010).

International Search Report and Written Opinion issued by the U.S. Patent and Trademark Office as International Searching Authority for International Application No. PCT/US2013/049265 dated Dec. 23, 2013 (9 pages).

Mosier, N., et al., "Features of promising technologies for pretreatment of lignocellulosic biomass,". Bioresource Technology, vol. 96, pp. 673-686 (2005).

Kang, S. W., et al., "Production of cellulases and hemicellulases by Aspergillus niger KK2 from lignocellulosic biomass," Bioresource Technology, vol. 91, pp. 153-156 (2004).

Moreau, C., et al., "Selective preparation of furfural from xylose over microporous solid acid catalysts," Industrial Crops and Products, vol. 7, pp. 95-99 (1998).

Dias, A. S., et al., "Modified versions of sulfated zirconia as catalysts for the conversion of xylose to furfural," Catalysis Letters, vol. 114, No. 3-4, pp. 151-160 (Apr. 2007).

International Search Report and Written Opinion issued in PCT/US2014/021609, dated May 22, 2014 (9 pages).

Extended European Search Report issued in EP14759993.0, dated Apr. 28, 2016 (6 pages).

English translation of Search Report issued by the Eurasian Patent Office in EA Patent No. 201591308, completed Feb. 19, 2016 (1 page).

Search Report issued by the Intellectual Property Office of Singapore in SG Patent No. 11201502353T, completed Apr. 20, 2016 (2 pages).

Written Opinion issued by the Intellectual Property Office of Singapore in SG Patent No. 11201502353T, Completed Dec. 17, 2016 (5 pages).

\* cited by examiner

RECONFIGURABLE PROCESSING ENCLOSURES

CROSS REFERENCE TO RELATED APPLICATIONS

This application is a continuation of U.S. application Ser. No. 14/299,005, filed Jun. 9, 2014, which is a continuation of PCT/US 14/21629 filed Mar. 7, 2014 which claims priority to the following provisional applications: U.S. Ser. No. 61/774,684, filed Mar. 8, 2013; U.S. Ser. No. 61/774,773, filed Mar. 8, 2013; U.S. Ser. No. 61/774,731, filed Mar. 8, 2013; U.S. Ser. No. 61/774,735, filed Mar. 8, 2013; U.S. Ser. No. 61/774,740, filed Mar. 8, 2013; U.S. Ser. No. 61/774,744, filed Mar. 8, 2013; U.S. Ser. No. 61/774,746, filed Mar. 8, 2013; U.S. Ser. No. 61/774,750, filed Mar. 8, 2013; U.S. Ser. No. 61/774,752, filed Mar. 8, 2013; U.S. Ser. No. 61/774,754, filed Mar. 8, 2013; U.S. Ser. No. 61/774,775, filed Mar. 8, 2013; U.S. Ser. No. 61/774,780, filed Mar. 8, 2013; U.S. Ser. No. 61/774,761, filed Mar. 8, 2013; U.S. Ser. No. 61/774,723, filed Mar. 8, 2013; and U.S. Ser. No. 61/793,336, filed Mar. 15, 2013. The full disclosure of each of these applications is incorporated by reference herein.

BACKGROUND OF THE INVENTION

Many potential lignocellulosic feedstocks are available today, including agricultural residues, woody biomass, municipal waste, oilseeds/cakes and seaweed, to name a few. At present, these materials are often under-utilized, being used, for example, as animal feed, biocompost materials, burned in a co-generation facility or even landfilled.

Lignocellulosic biomass includes crystalline cellulose fibrils embedded in a hemicellulose matrix, surrounded by lignin. This produces a compact matrix that is difficult to access by enzymes and other chemical, biochemical and/or biological processes. Cellulosic biomass materials (e.g., biomass material from which the lignin has been removed) is more accessible to enzymes and other conversion processes, but even so, naturally-occurring cellulosic materials often have low yields (relative to theoretical yields) when contacted with hydrolyzing enzymes. Lignocellulosic biomass is even more recalcitrant to enzyme attack. Furthermore, each type of lignocellulosic biomass has its own specific composition of cellulose, hemicellulose and lignin.

SUMMARY

Generally, the inventions related to enclosures for treating materials, such as biomass. The inventions also relate to equipment, methods and systems for producing products from materials, such as a biomass material. Increasing the throughput and safety, and reducing the costs associated with treatment of biomass are important goals in the development of useful and flexible manufacturing processes. In methods involving irradiation, hazards can be mitigated by enclosing the irradiation in a vault. For example, the vault can be constructed of easy to assemble and re-configurable radiation opaque parts or units such as concrete of sufficient thickness. Generally, the methods disclosed herein include treating a recalcitrant biomass with electron beams in a vault and then biochemically and chemically processing the reduced recalcitrance material to, for example, ethanol, xylitol and other products.

In one aspect, the invention relates to a material (e.g., biomass) treatment facility including a vault with walls, ceiling, and a foundation. Within the vault can be contained/placed a material conveying system (e.g., a vibratory conveyor) configured to convey a material (e.g., a biomass material or a hydrocarbon containing material), through a radiation field, such as under an electron beam. Optionally, each of the walls can include a plurality of discrete units and, optionally, the ceiling can also include a plurality of discrete units. In some cases, the walls, ceiling and foundation include concrete, such as concrete selected from the group consisting of regular concrete, high density concrete, pre-tensioned concrete, lead containing concrete, rebar containing concrete and combinations of these.

In some implementations, the electron irradiation device is supported by the ceiling of the vault. In some cases, the electron irradiation device can weigh at least 5 Tons (e.g., at least 6 tons, at least 7 tons, at least 8 tons, at least 9 tons, at least 10 tons, between about 5 and 20 tons).

In some implementations, the vault includes a door that is substantially radiation opaque, e.g., constructed with materials including lead and steel. Optionally, the door includes a steel interior in contact with a front and back layer that includes lead.

In some cases, the vault is re-configurable. Optionally, the walls include interlocking blocks and/or the ceiling comprises ceiling panels In some implementations, the walls of the vault are configured to support a network of I-beams. The network of I-beams can support a ceiling, for example ceiling panels or other ceiling units.

In some implementations, the walls, ceiling and foundation, are at least 4 feet thick (e.g., at least 5 feet thick, at least 6 feet thick, between 5 and 10 feet thick). Optionally the facility includes a foundation including a concrete slab. Optionally several slabs are utilized in a facility.

In some implementations, the facility includes an opening for continuously supplying biomass into the vault and to the conveyor. Optionally, the facility also includes openings for a continuous loop conveyor for continuously removing biomass from the conveyor and out of the vault.

In another aspect, the invention relates to a method of treating a material (e.g., a biomass material, a hydrocarbon containing material). The method includes irradiating the material with an electron beam, in a vault with a foundation, walls and a ceiling. Optionally each of the walls includes a plurality of discrete units and, optionally the ceiling includes a plurality of discrete units.

In some instances, the biomass material that is treated is a lignocellulosic material in the form of wood or laminate. In some other instances, the material to be treated is selected from the group consisting of wood, particle board, sawdust, agricultural waste, sewage, silage, grasses, rice hulls, bagasse, cotton, jute, hemp, flax, bamboo, sisal, abaca, straw, corn cobs, corn stover, switchgrass, alfalfa, hay, coconut hair, seaweed, algae and mixtures thereof.

Optionally, the vault is re-configurable. In some instances, the vault is re-configured after irradiating the biomass and then a second biomass is irradiated in the re-configured vault.

In some implementations, the walls of the vault used for treating the biomass material include interlocking concrete blocks. Optionally the walls support a network of I-beams and the network of I-beams support the ceiling (e.g., discrete ceiling panels or other ceiling units) as well as the irradiator. In some cases, the walls, ceiling and foundation include concrete and the concrete can be regular concrete, high density concrete, pre-tensioned concrete, lead containing concrete, rebar containing concrete and combinations of these.

One of the advantages of using discrete units for the building of structures, e.g., vaults, as used in the methods disclosed herein, is that damaged units can be easily replaced. Another advantage is that modifications of the structure to accommodate process changes and changes in equipment needs can be relatively simple. The entire structure or structures can even be disassembled and reassembled (for example at a different location). Therefore, for example, the building structures are re-configurable, as new structures (e.g., different in shape and/or proportions) or similar (e.g., similar in shape and proportions) structures. Recycling of the material at the end of life of the structures can also be facilitated, and/or the units can be sold or repurposed for other structural uses. In addition, the value of the real estate is maintained, since after disassembling and removing the structures, the land is returned to its original state.

Implementations of the invention can optionally include one or more of the following summarized features. In some implementations, the selected features can be applied or utilized in any order while in other implementations a specific selected sequence is applied or utilized. Individual features can be applied or utilized more than once in any sequence and even continuously. In addition, an entire sequence, or a portion of a sequence, of applied or utilized features can be applied or utilized once, repeatedly or continuously in any order. In some optional implementations, the features can be applied or utilized with different, or where applicable the same, set or varied, quantitative or qualitative parameters as determined by a person skilled in the art. For example, parameters of the features such as size, individual dimensions (e.g., length, width, height), location of, degree (e.g., to what extent such as the degree of recalcitrance), duration, frequency of use, density, concentration, intensity and speed can be varied or set, where applicable as determined by a person of skill in the art.

Features, for example, include: a treatment facility including a vault having walls, ceiling and a foundation; a vault maintained at an internal pressure different than nominal atmospheric pressure; a vault maintained at an internal pressure lower than atmospheric pressure; a vault having within it a conveying system configured to convey biomass under an electron beam; a vault with walls that include a plurality of discrete units; a vault with a ceiling that includes a plurality of discrete units; a vault that is re-configurable; an electron irradiation device supported by the ceiling of a vault and disposed to irradiate biomass conveyed by a conveying system; an electron irradiation device weighting at least 5 tons supported by the ceiling of a vault and disposed to irradiate biomass conveyed by a conveying system; an electron irradiation device weighting at least 10 tons supported by the ceiling of a vault and disposed to irradiate biomass conveyed by a conveying system; an electron irradiation device weighting between about 5 and 20 tons supported by the ceiling of a vault and disposed to irradiate biomass conveyed by a conveying system; a vault that includes a foundation that comprises a concrete slab: a vault wherein the walls include interlocking blocks; a vault wherein the walls support a network of I-beams and the network of I-beam supports ceiling panels; a vault wherein the walls, ceiling and foundation are at least 4 feet thick; a vault wherein the walls, ceiling and foundation are at least 5 feet thick; a vault wherein the walls, ceiling and foundation are between about 5 and about 10 feet thick; a vault wherein the walls are coated with corrosion resistant materials; a vault wherein the walls are covered with stainless steel sheeting; a vault wherein the walls include regular concrete; a vault wherein the walls include high density concrete; a vault wherein the walls include pre-tensioned concrete; a vault wherein the wall include lead containing concrete; a vault wherein the walls include rebar containing concrete; a vault wherein the ceiling includes regular concrete; a vault wherein the ceiling includes high density concrete; a vault wherein the ceiling includes pre-tensioned concrete; a vault wherein the ceiling includes lead containing concrete; a vault wherein the ceiling includes rebar containing concrete; a vault wherein the foundation includes regular concrete; a vault wherein the foundation includes high density concrete; a vault wherein the foundation includes pre-tensioned concrete; a vault wherein the foundation includes lead containing concrete; a vault wherein the foundation includes rebar containing concrete; a vault that includes a substantially radiation opaque door, a treatment facility including a vault and a substantially radiation opaque door to the vault; a vault including a substantially radiation opaque door, the door comprising a steel interior in contact with a front and back layer comprising lead; a vault including and an opening for continuously supplying biomass into the vault and to a conveyor, an openings for a continuous loop conveyor for continuously removing biomass from the conveyor and out of the vault; irradiating a lignocellulosic biomass with an electron beam, in a treatment facility that includes a vault; irradiating a lignocellulosic biomass with an electron beam, in a treatment facility that includes a vault, re-configuring the vault and irradiating a second biomass material in the re-configured vault; irradiating wood with an electron beam, in a treatment facility that includes a vault; irradiating a laminate with an electron beam, in a treatment facility that includes a vault; irradiating a particle board with an electron beam, in a treatment facility that includes a vault; irradiating sawdust with an electron beam, in a treatment facility that includes a vault; irradiating agricultural waste with an electron beam, in a treatment facility that includes a vault; irradiating sewage with an electron beam, in a treatment facility that includes a vault; irradiating silage with an electron beam, in a treatment facility that includes a vault; irradiating grasses with an electron beam, in a treatment facility that includes a vault; irradiating rice hulls with an electron beam, in a treatment facility that includes a vault; irradiating bagasse with an electron beam, in a treatment facility that includes a vault; irradiating cotton with an electron beam, in a treatment facility that includes a vault; irradiating jute with an electron beam, in a treatment facility that includes a vault; irradiating hemp with an electron beam, in a treatment facility that includes a vault; irradiating flax with an electron beam, in a treatment facility that includes a vault; irradiating bamboo with an electron beam, in a treatment facility that includes a vault; irradiating sisal with an electron beam, in a treatment facility that includes a vault; irradiating abaca with an electron beam, in a treatment facility that includes a vault; irradiating straw with an electron beam, in a treatment facility that includes a vault; irradiating corn cobs with an electron beam, in a treatment facility that includes a vault; irradiating corn stover with an electron beam, in a treatment facility that includes a vault; irradiating switchgrass with an electron beam, in a treatment facility that includes a vault; irradiating alfalfa with an electron beam, in a treatment facility that includes a vault; irradiating hay with an electron beam, in a treatment facility that includes a vault; irradiating coconut hair with an electron beam, in a treatment facility that includes a vault; irradiating seaweed with an electron beam, in a treatment facility that includes a vault; irradiating algae with an electron beam, in a treatment facility that includes a vault; a treatment facility that includes a vault and a vibratory conveyor therein for conveying biomass.

Other features and advantages of the invention will be apparent from the following detailed description, and from the claims.

DESCRIPTION OF THE DRAWING

FIG. 5A is a perspective exploded view of two discrete units that may be used to build a vault, while

DETAILED DESCRIPTION

Figure 1:
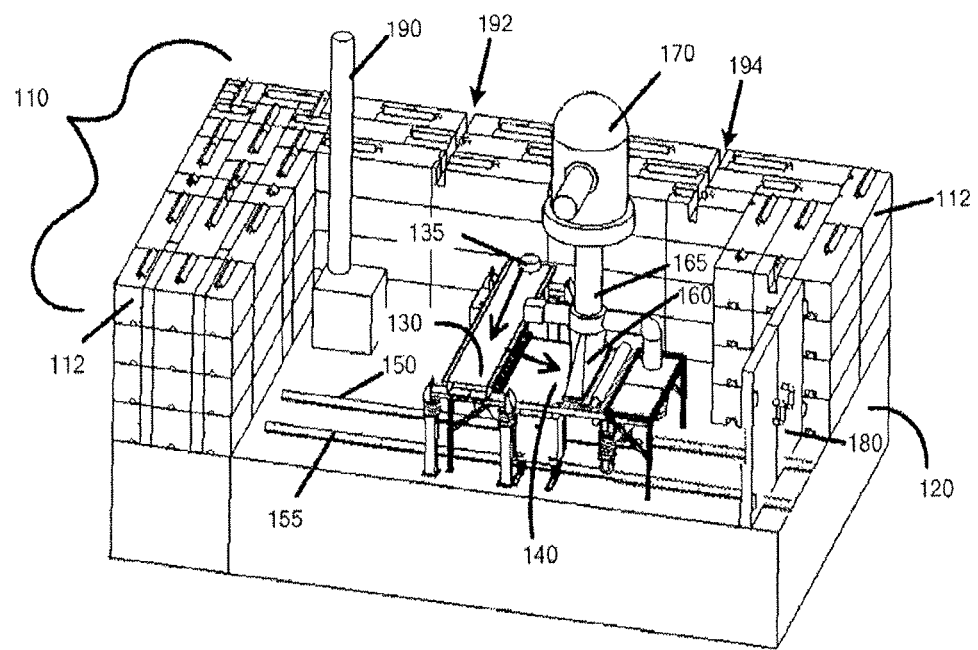
FIG. 1 is a perspective view of a vault, with the ceiling, floor, and front wall cut away to show the interior.

Using the methods and systems described herein, cellulosic and lignocellulosic feedstock materials, for example that can be sourced from biomass (e.g., plant biomass, animal biomass, paper, and municipal waste biomass) and that are often readily available but difficult to process, can be turned into useful products (e.g., sugars such as xylose and glucose, and alcohols such as ethanol and butanol). Included are methods and systems for treating materials such as biomass with radiation in a vault constructed with discrete units.

For examples processes for manufacturing sugar solutions and products derived therefrom are described herein. These processes may include, for example, optionally mechanically treating a cellulosic and/or lignocellulosic feedstock. Before and/or after this treatment, the feedstock can be treated with another physical treatment, for example irradiation, steam explosion, pyrolysis, sonication and/or oxidation to reduce, or further reduce its recalcitrance. A sugar solution is formed by saccharifying the feedstock by, for example, by the addition of one or more enzymes. A product can be derived from the sugar solution, for example, by fermentation to an alcohol. Further processing can include purifying the solution, for example by distillation. If desired, the steps of measuring lignin content and setting or adjusting process parameters (e.g., irradiation dosage) based on this measurement can be performed at various stages of the process, for example, as described in U.S. Pat. No. 8,415, 122 issued Apr. 9, 2013, the complete disclosure of which is incorporated herein by reference.

Since the recalcitrance reducing step can be a high energy process, the treatment can be performed in a vault to contain the energy or products derived for the energetic process. For example, the vault can be configured to contain heat energy, electrical energy, radiation energy, explosion energy, gases and combinations of these.

If the treatment methods for reducing the recalcitrance include irradiation of the feedstock, the vault can be made of radiation opaque materials. Several processes can occur in biomass when electrons from an electron beam interact with matter in inelastic collisions. For example, ionization of the material, chain scission of polymers in the material, cross linking of polymers in the material, oxidation of the material, generation of X-rays ("Bremsstrahlung") and vibrational excitation of molecules (e.g., phonon generation).

Without being bound to a particular mechanism, the reduction in recalcitrance can be due to several of these inelastic collision effects, for example ionization, chain scission of polymers, oxidation and phonon generation. Some of the effects (e.g., especially X-ray generation), necessitate shielding and engineering barriers, for example, enclosing the irradiation processes in a vault made of concrete or other radiation opaque material(s). Another effect of irradiation, vibrational excitation, is equivalent to heating up the sample and can cause the release of volatile organic compounds (VOCs). In addition, if the irradiation occurs in air, ozone can be generated. Confining the irradiation process in a vault therefore can also mitigate undesired exposure to ozone and VOCs.

Figure 2:
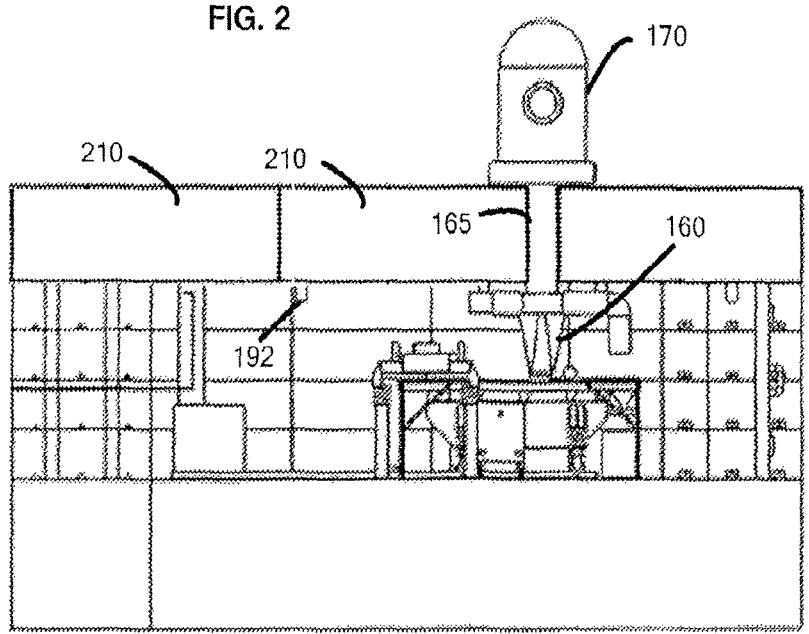
FIG. 2 is a side view of the vault shown in FIG. 1, with the ceiling added.

FIG. 1 is a perspective view of a vault for irradiating a material (e.g., a biomass material) showing some aspects of the structure. For example the walls 110 include discrete units, for example 112. The walls are built on a concrete slab 120. The vault contains a biomass conveying system with two conveyors 130 and 140, which are generally perpendicular to each other. The conveyors can be covered or enclosed vibratory conveyors, and conveyor 130 can have a cross-cut outlet onto the second conveyor 140. The conveyors and/or any other equipment can be mounted on tracks 150 and 155. The tracks are mounted to the concrete floor and can extend out of the vault to the exterior or to another structure (e.g., another vault). Parts of the irradiation devices are shown, for example scan horn 160, vacuum channel or gate 165 and electron accelerator 170. The irradiation device is supported by the ceiling which is not shown in FIG. 1 but is depicted in FIG. 2. The vault includes door 180 constructed of radiation opaque materials (e.g., lead and steel). The vault also includes other openings such as for conveying biomass into the vaults e.g., pipes included as a part of a pneumatic conveyor connected to the conveyor 130 inlet 135 and conveyor 140 outlet (not shown in this figure). Ventilation openings, for example for pipe 190 can also be included. Slots in the walls can accommodate I-beams (e.g., H-beams) that are configured for supporting the ceiling, for example slots 192 and 194. In general, the systems are constructed so that there are no "daylight" openings. For example, the openings are such that there is no straight path for any radiation to travel through. Optionally, avoiding daylight openings can be accomplished by having the openings that go through one or more change in path, such as one or more 90 degree bend in the pathway of any pipes or conduits leading in or out of the vaults. The openings or conduits can also be lined or made thicker with lead, for example in addition to having bends in the pathways of these conduits, to aid in stopping any radiation from escaping. To improve the life of the structures, the interior surfaces (e.g., of concrete blocks) can be coated or covered with a corrosion resistant material, such as stainless steel.

The vaults can be designed to contain any process gases, e.g., wherein the walls have reduced porosity to any gases. The porosity of the walls can be reduced by infusion of materials into blocks. For example, concrete with lower permeability can generally be achieved by substituting between 25 to 65 percent slag cement for Portland cement. Finely-divided solids (e.g., lime, silicates and colloidal silica) add to the cement when the blocks are made can reduce permeability to water and gases by increasing the density or by filling up voids. Some crystalline admixtures react with water and cement particles in the concrete to form calcium silicate hydrates and/or pore-blocking precipitates in the existing microcracks and capillaries. The resulting crystalline deposits, which are analogous to calcium silicate hydrate formation, become integrally bound with the hydrated pastes. Porosity reducing additives can also include hydrophobic water-repellent chemicals based on soaps and long-chain fatty acids derivatives, vegetable oils (tallows, soya-based materials, and greases), and petroleum (mineral oil, paraffin waxes, and bitumen emulsions). These materials are more useful for providing a water repellency layer on the material and would be more usefully applied to the exterior portions of the vault to aid in decreasing interior vault humidity, which can exacerbate corrosion in the vault.

FIG. 2 is a side view of the vault shown in FIG. 1, with the ceiling added. FIG. 2 shows concrete ceiling tiles 210 that are supported by an I-beam lattice, spider or web (see FIG. 4A). The electron accelerator 170 is mounted on the ceiling outside of the vault. A stainless steel vacuum channel provides a high vacuum path for the electrons to travel from the accelerator located outside of the vault to the interior of the vault and includes a tube 165, The tube 165 passes through the ceiling and is functionally connected to the accelerator 170 and to the scan horn 160.

Figure 3:
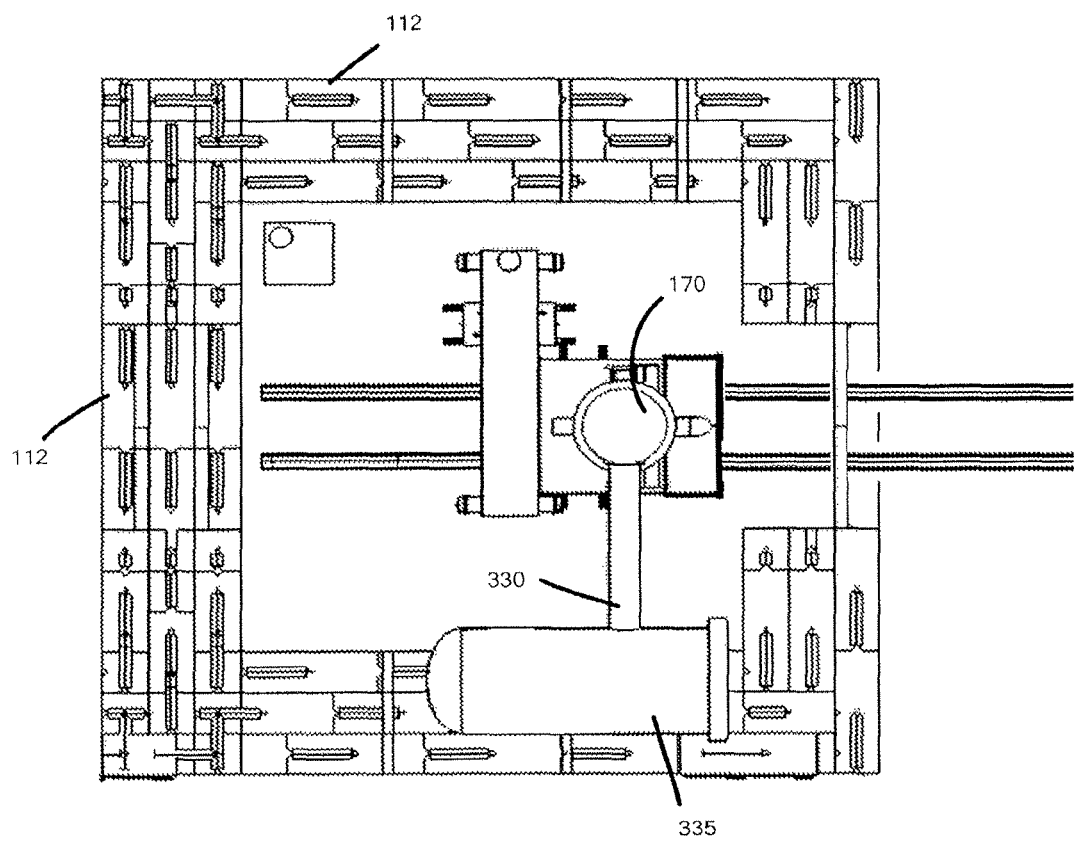
FIG. 3 is a top view of a vault shown in FIG. 1.

FIG. 3 is a top side view of the vault shown in FIGS. 1 and 2. The ceiling is not included in the figure so that components in the vault and the walls can be seen. Discrete units of the walls are clearly shown, for example 112. The electron accelerator 170 is shown in electrical connection through electric conduit 330 to a power source 335 (e.g., to provide a high voltage to the accelerator). The tracks 150 and 155 are shown extending out of the vault.

Figure 4A:
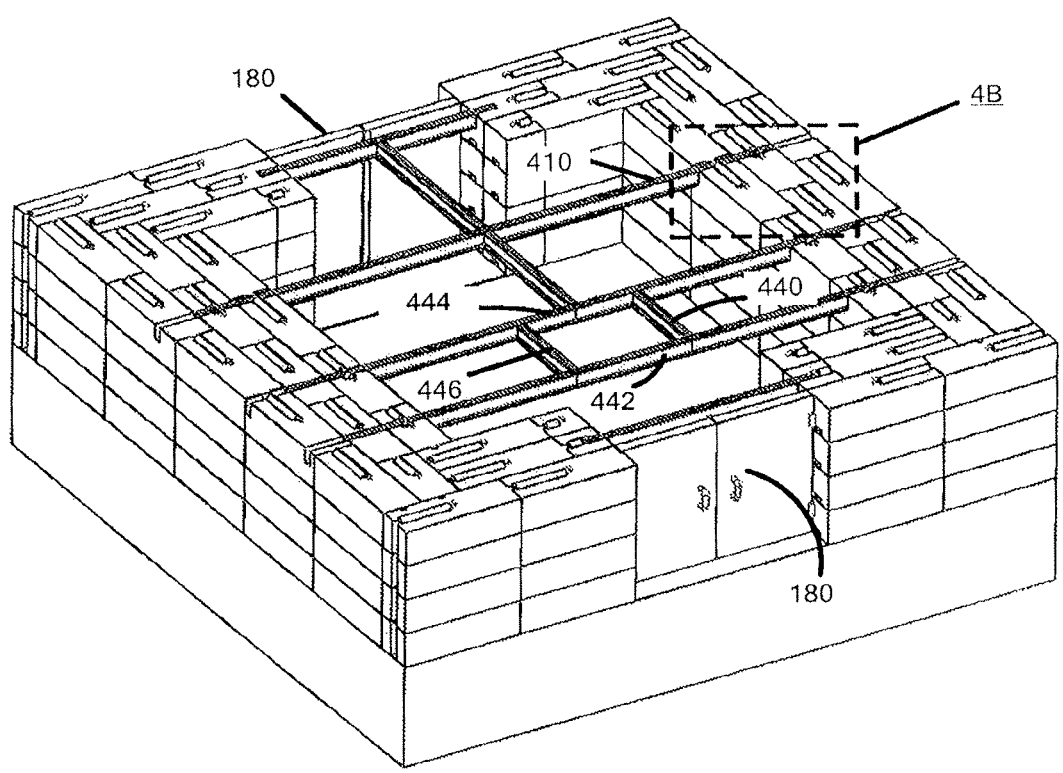
FIG. 4A is a perspective view of a vault, shown without its interior components.
Figure 4B:
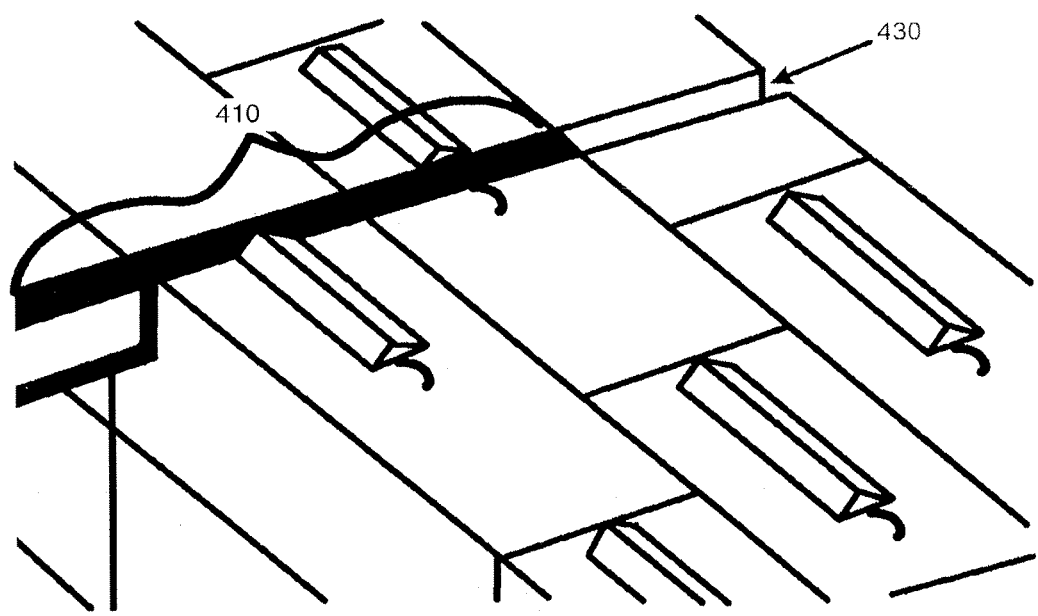
FIG. 4B is an enlarged detail view of a wall of the vault.

FIG. 4A is a perspective view of a vault for irradiating a material (e.g., a biomass material). The vault is similar to the vault shown in FIGS. 1-3 except that the vault has extra doors (e.g., doors 180 at opposite sides of the vault). A possible arrangement of I-beams that supports the ceiling is shown. The walls have slots to insert the I-beams into. FIG. 4B is an enlarged detail view of a wall of the vault shown in FIG. 4A. FIG. 4B shows an I-beam 410 placed in the slot 430. In this embodiment the walls can be 6 feet thick, the I-beams can be 10 by 5 inches, the ceiling tiles can be 4 feet thick, and the outer perimeter of the vault can be 34 by 34 square feet. In order to support the irradiator and ceiling tiles, I-beams 440, 442, 444, and 446 are arranged is a tight square 6 by 6 feet. Using the above listed measurements and the configuration outlined for the vault depicted by FIG. 4A, finite element analysis shows that the arrangement allows support of the ceiling tiles and a 10 ton irradiator.

Figure 4C:
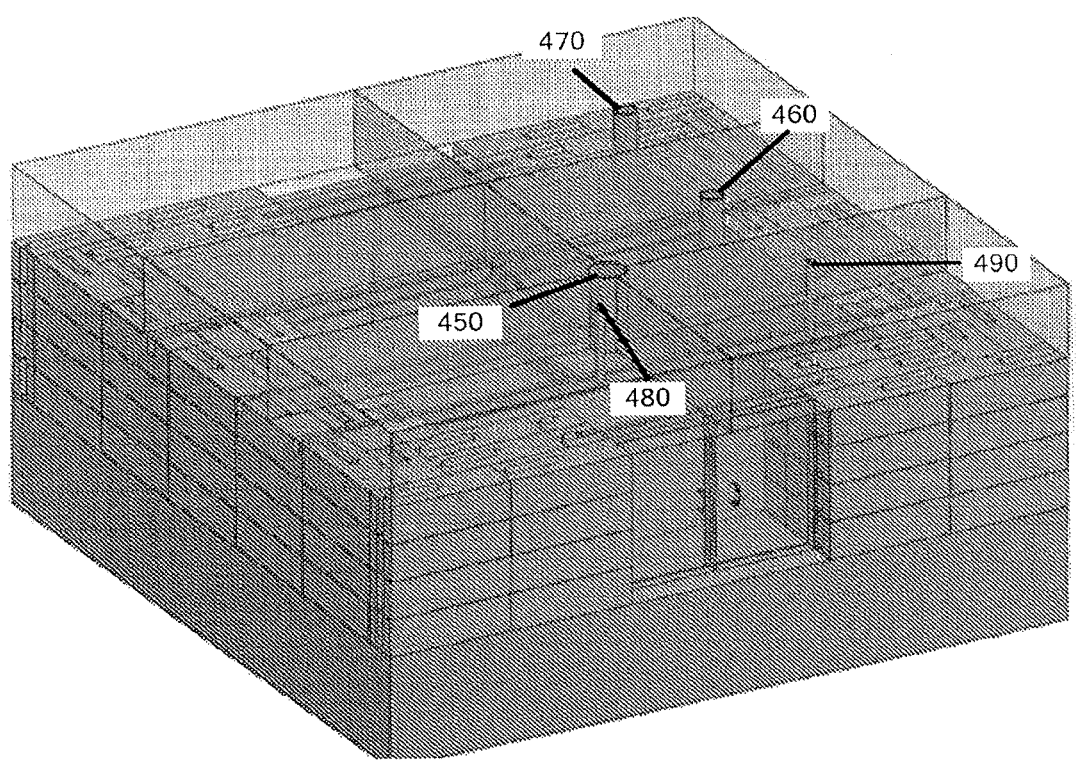
FIG. 4C is a perspective view of the vault with the ceiling and various conduits shown.

FIG. 4C is a perspective view of the vault depicted in FIG. 4A with the ceiling tiles shown in outline. This view excludes the irradiation device and other equipment such as tubes to more clearly show the wall units, concrete slab and ceiling tiles. An opening 450 for a vacuum channel (for example the channel 165 as previously described) is shown. The opening 470 can be for a ventilation system, example with optional pollution control systems. The opening 460 can be for a conduit (e.g., an inlet to the vault for biomass) in communication with the conveyor 130 through inlet 135. The openings 480 and 490 can be openings for a continuous loop conveyor system (e.g., pneumatic conveyor) used for removing the biomass after treatment.

Figure 5A:
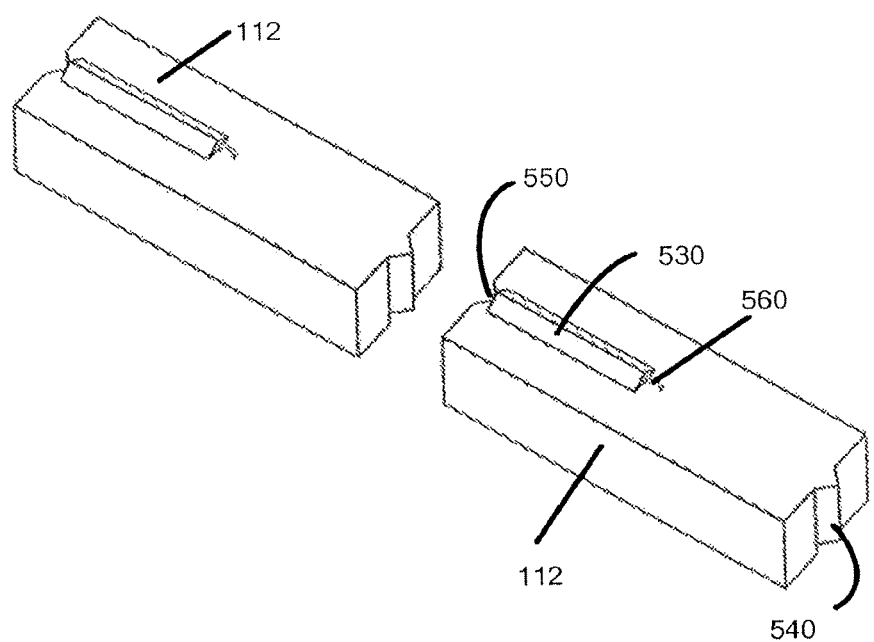
Figure 5B:
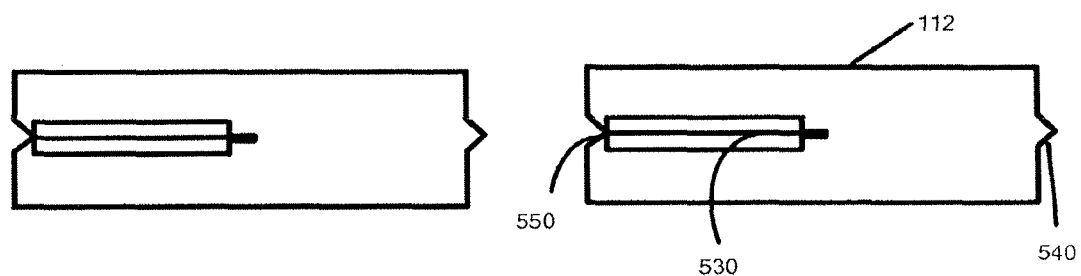
FIG. 5B is a top view of the units.

FIG. 5A is a perspective exploded view showing two discrete units 112 that can be used for building the walls of a vault. Each of the units include tongues and grooves that help align the units during assembly and keep the units aligned once they have been built into a structure. In the example shown, the units include a top tongue 530, side tongue 540, and side groove 550. The units can also include a loop 560 for attachment with a hook (e.g., formed of steel) that can aid in lifting the unit. FIG. 5B is a top side view showing the same elements. A bottom side view of 112 would be similar to the top side view except that the tongues 530 would be replaced by corresponding grooves (e.g., the lower surface would include an indentation into the unit rather than a protrusion).

In addition to the units as shown in FIG. 5, the discrete units can be a variety of other interlocking shapes. For example, their two dimensional projection can be selected from the 17 translational symmetry groups or they may be a more random arrangement of interlocking units or combination of units. The tongue and groove can be replace with other methods of fixing the units in place, for example external fasteners, binders, adhesives, mortar, dowels (e.g., made with re-bar), complementary joining methods such as mortise and tendon, dovetail joints and/or finger joints. Some of the units can be specially machined or designed for a specific purpose, for example grooved as previously discussed to support an I-beam, have holes cut into them to accommodate conveying systems (e.g., pipes, conveyors) and/or be fit with fasteners (e.g., hinges, hooks, bolts). The ceiling units can be likewise designed into various interlocking shapes.

The vaults used for irradiation of materials are preferably constructed of structurally resilient and radiation opaque materials, for example concrete, stainless steel, lead, dirt and combinations of these can be utilized. Concrete, for example can be regular concrete, high density concrete, pre-tensioned concrete, lead containing concrete, re-bar containing concrete and combinations of these. For example the radiation halving thickness of concrete is about 2.4 Inches so at 4 feet thick the radiation will be reduced by at least 1 million times the original strength. For a dose of 250 kGy applied inside the structure, the resulting radiation outside the structure, assuming an F-factor of 1.0, will be 0.25 microrem, well below safe limits. The thickness of the vault can be modified as needed. For example the wall thickness can be at least two feet thick (e.g., at least 3 feet, at least 4 feet, at least 5 feet, at least 6 feet, between about 2 and 12 feet, between about 4 and 10 feet, between about 4 and 8 feet). In addition to walls, floors and ceilings, the vaults can have doors made of radiation opaque materials. The materials can be layered, for example, doors can be made as layers of about 1" lead over about 6" of steel over about 1" of lead.

With respect to structural resilience, the vaults are preferably designed to withstand usual and unusual outdoor elements. For example, the vaults should be able to withstand a seismic input of at least 6, tsunamis, hurricanes, tornados and flooding.

The vaults can be built on a concrete slab. Since the entire structure including associated equipment can be very heavy (e.g., greater than 10 tons, greater than about 20 tons, greater than about 30 tons, greater than about 40 tons, greater than about 50 tons, greater than about 100 tons, greater than about 500 tons) the concrete slab needs to be at least 4 feet thick (e.g. at least 5 feet, at least 6 feet, between 4 and 20 feet, between about 4 and 10 feet). In addition, the concrete slab can be reinforced by metal rods (e.g., rebar).

Walls can be made from concrete blocks, e.g., interlocking concrete blocks. For example, the concrete can include Portland cement, sand, water, rebar, lead, construction aggregates (e.g., crushed stone, gravel, steel, slag, recycled concrete, geosynthetic aggregate, large aggregate, small aggregate) and combinations of these. The compressive strength of the blocks should be between about 2500 and 6000 psi (e.g., between about 3000 and 5000 psi, between about 3500 and 4500 psi, between about 4000 and 5000 psi). The flexural strength of the blocks can be between about 500 psi and 1500 psi (e.g., between about 500 and 1000 psi, between about 550 psi and 800 psi). The density can be at least about 1500 kg/m$^3$ (e.g., at least about 2000 kg/m$^3$, at least about 2500 kg/m$^3$, at least about 3000 kg/m$^3$, at least about 3500 kg/m$^3$, at least about 4000 kg/m$^3$, at least about 4500 kg/m$^3$, at least about 5000 kg/m$^3$, or even high, e.g., at least about 6000 kg/m$^3$, at least about 7000 kg/m$^3$, at least about 8000 kg/m$^3$, at least about 9000 kg/m$^3$). Preferably the blocks are made utilizing high density concrete, for example that can be from natural heavyweight aggregates such as barites or magnetite which typically give densities of between about 3500 kg/m$^3$ and 4000 kg/m$^3$ respectively. In some embodiments iron or lead can replace at least a portion of the aggregates giving even greater densities, for example 5900 kg/m$^3$ for iron or 8900 kg/m$^3$ for lead.

The volume of each discrete unit can be between about 6 ft$^3$-50 ft$^3$ (e.g. between about 8-24). Preferably, the blocks are generally rectangular in shape, for example about 2 feet high by 6 feet wide by 2 feet deep, 2 feet high by 5 feet wide by 2 feet deep, 2 feet high by 4 feet wide by 2 feet deep, 2 feet high by 3 feet wide by 2 feet deep, 2 feet high by 2 feet wide by 2 feet deep. The blocks can also be much larger, for example shaped as sheets and/or slabs with larger volumes (e.g., between about 50 and 200 cubic ft) for example about 10 feet high by 6 feet wide by 2 feet deep, 6 feet high by 6 feet wide by 2 feet deep, 4 feet high by 6 feet wide by 2 feet deep. For example MEGASHIELD™ Modular Concrete Block System from Nelco (Burlington, Mass.) can be used.

The vaults can be configured or re-configured into any useful shape. For example the vaults can be dome shaped, pyramidal in shape, tetragonal in shape, cone shaped, cube shaped, triangular prism shaped, rectangular prism, and combinations of these. Several of the vaults can share common walls. The vaults can also optionally be arranged into an array of vaults. Once a vault has been made into a desired shape, it can be used for a time and, optionally, can then be modified (e.g., re-configured) by addition of more discrete units and/or re-assembling part or all of the discrete units into a different configuration. For example, a tetragonal shaped vault can be re-configured into a cube shaped vault.

The vaults can be partially or fully immersed in dirt, bedrock, clay, sand and/or water. The vaults can be built to be transported from site to site, for example as part of a biomass processing facility as described in U.S. Pat. No. 8,318,453 the entire disclosure therein herein incorporated by reference.

Some more details and reiterations of processes, equipment or systems for treating a feedstock that can be utilized, for example, with the embodiments already discussed above, or in other embodiments, are described in the following disclosures.

Radiation Treatment

The feedstock can be treated with radiation to modify its structure to reduce its recalcitrance. Such treatment can, for example, reduce the average molecular weight of the feedstock, change the crystalline structure of the feedstock, and/or increase the surface area and/or porosity of the feedstock. Radiation can be by, for example electron beam, ion beam, 100 nm to 280 nm ultraviolet (UV) light, gamma or X-ray radiation. Radiation treatments and systems for treatments are discussed in U.S. Pat. No. 8,142,620 and U.S. patent application Ser. No. 12/417,731, the entire disclosures of which are incorporated herein by reference.

Each form of radiation ionizes the biomass via particular interactions, as determined by the energy of the radiation. Heavy charged particles primarily ionize matter via Coulomb scattering; furthermore, these interactions produce energetic electrons that may further ionize matter. Alpha particles are identical to the nucleus of a helium atom and are produced by the alpha decay of various radioactive nuclei, such as isotopes of bismuth, polonium, astatine, radon, francium, radium, several actinides, such as actinium, thorium, uranium, neptunium, curium, californium, americium, and plutonium. Electrons interact via Coulomb scattering and bremsstrahlung radiation produced by changes in the velocity of electrons.

When particles are utilized, they can be neutral (uncharged), positively charged or negatively charged. When charged, the charged particles can bear a single positive or negative charge, or multiple charges, e.g., one, two, three or even four or more charges. In instances in which chain scission is desired to change the molecular structure of the carbohydrate containing material, positively charged particles may be desirable, in part, due to their acidic nature. When particles are utilized, the particles can have the mass of a resting electron, or greater, e.g., 500, 1000, 1500, or 2000 or more times the mass of a resting electron. For example, the particles can have a mass of from about 1 atomic unit to about 150 atomic units, e.g., from about 1 atomic unit to about 50 atomic units, or from about 1 to about 25, e.g., 1, 2, 3, 4, 5, 10, 12 or 15 atomic units.

Gamma radiation has the advantage of a significant penetration depth into a variety of material in the sample.

In embodiments in which the irradiating is performed with electromagnetic radiation, the electromagnetic radiation can have, e.g., energy per photon (in electron volts) of greater than 10$^2$ eV, e.g., greater than 10$^3$, 10$^4$, 10$^5$, 10$^6$, or even greater than 10$^7$ eV. In some embodiments, the electromagnetic radiation has energy per photon of between 10$^4$ and 10$^7$, e.g., between 10$^5$ and 10$^6$ eV. The electromagnetic radiation can have a frequency of, e.g., greater than 10$^{16}$ Hz, greater than 10$^{17}$ Hz, 10$^{18}$, 10$^{19}$, 10$^{20}$, or even greater than 10$^{21}$ Hz. In some embodiments, the electromagnetic radiation has a frequency of between 10$^{18}$ and 10$^{22}$ Hz, e.g., between 10$^{19}$ to 10$^{21}$ Hz.

Electron bombardment may be performed using an electron beam device that has a nominal energy of less than 10 MeV, e.g., less than 7 MeV, less than 5 MeV, or less than 2 MeV, e.g., from about 0.5 to 1.5 MeV, from about 0.8 to 1.8 MeV, or from about 0.7 to 1 MeV. In some implementations the nominal energy is about 500 to 800 keV.

The electron beam may have a relatively high total beam power (the combined beam power of all accelerating heads, or, if multiple accelerators are used, of all accelerators and all heads), e.g., at least 25 kW, e.g., at least 30, 40, 50, 60, 65, 70, 80, 100, 125, or 150 kW. In some cases, the power is even as high as 500 kW, 750 kW, or even 1000 kW or more. In some cases the electron beam has a beam power of 1200 kW or more, e.g., 1400, 1600, 1800, or even 3000 kW.

This high total beam power is usually achieved by utilizing multiple accelerating heads. For example, the electron beam device may include two, four, or more accelerating heads. The use of multiple heads, each of which has a relatively low beam power, prevents excessive temperature rise in the material, thereby preventing burning of the material, and also increases the uniformity of the dose through the thickness of the layer of material.

It is generally preferred that the bed of biomass material has a relatively uniform thickness. In some embodiments the thickness is less than about 1 inch (e.g., less than about 0.75 inches, less than about 0.5 inches, less than about 0.25 inches, less than about 0.1 inches, between about 0.1 and 1 inch, between about 0.2 and 0.3 inches).

It is desirable to treat the material as quickly as possible. In general, it is preferred that treatment be performed at a dose rate of greater than about 0.25 Mrad per second, e.g., greater than about 0.5, 0.75, 1, 1.5, 2, 5, 7, 10, 12, 15, or even greater than about 20 Mrad per second, e.g., about 0.25 to 2 Mrad per second. Higher dose rates allow a higher throughput for a target (e.g., the desired) dose. Higher dose rates generally require higher line speeds, to avoid thermal decomposition of the material. In one implementation, the accelerator is set for 3 MeV, 50 mA beam current, and the line speed is 24 feet/minute, for a sample thickness of about 20 mm (e.g., comminuted corn cob material with a bulk density of 0.5 g/cm$^3$).

In some embodiments, electron bombardment is performed until the material receives a total dose of at least 0.1 Mrad, 0.25 Mrad, 1 Mrad, 5 Mrad, e.g., at least 10, 20, 30 or at least 40 Mrad. In some embodiments, the treatment is performed until the material receives a dose of from about 10 Mrad to about 50 Mrad, e.g., from about 20 Mrad to about 40 Mrad, or from about 25 Mrad to about 30 Mrad. In some implementations, a total dose of 25 to 35 Mrad is preferred, applied ideally over a couple of passes, e.g., at 5 Mrad/pass with each pass being applied for about one second. Cooling methods, systems and equipment can be used before, during, after and in between radiations, for example utilizing a cooling screw conveyor and/or a cooled vibratory conveyor.

Using multiple heads as discussed above, the material can be treated in multiple passes, for example, two passes at 10 to 20 Mrad/pass, e.g., 12 to 18 Mrad/pass, separated by a few seconds of cool-down, or three passes of 7 to 12 Mrad/pass, e.g., 5 to 20 Mrad/pass, 10 to 40 Mrad/pass, 9 to 11 Mrad/pass. As discussed herein, treating the material with several relatively low doses, rather than one high dose, tends to prevent overheating of the material and also increases dose uniformity through the thickness of the material. In some implementations, the material is stirred or otherwise mixed during or after each pass and then smoothed into a uniform layer again before the next pass, to further enhance treatment uniformity.

In some embodiments, electrons are accelerated to, for example, a speed of greater than 75 percent of the speed of light, e.g., greater than 85, 90, 95, or 99 percent of the speed of light.

In some embodiments, any processing described herein occurs on lignocellulosic material that remains dry as acquired or that has been dried, e.g., using heat and/or reduced pressure. For example, in some embodiments, the cellulosic and/or lignocellulosic material has less than about 25 wt. % retained water, measured at 25° C. and at fifty percent relative humidity (e.g., less than about 20 wt. %, less than about 15 wt. %, less than about 14 wt. %, less than about 13 wt. %, less than about 12 wt. %, less than about 10 wt. %, less than about 9 wt. %, less than about 8 wt. %, less than about 7 wt. %, less than about 6 wt. %, less than about 5 wt. %, less than about 4 wt. %, less than about 3 wt. %, less than about 2 wt. %, less than about 1 wt. %, or less than about 0.5 wt. %.

In some embodiments, two or more ionizing sources can be used, such as two or more electron sources. For example, samples can be treated, in any order, with a beam of electrons, followed by gamma radiation and UV light having wavelengths from about 100 nm to about 280 nm. In some embodiments, samples are treated with three ionizing radiation sources, such as a beam of electrons, gamma radiation, and energetic UV light. The biomass is conveyed through the treatment zone where it can be bombarded with electrons.

It may be advantageous to repeat the treatment to more thoroughly reduce the recalcitrance of the biomass and/or further modify the biomass. In particular the process parameters can be adjusted after a first (e.g., second, third, fourth or more) pass depending on the recalcitrance of the material. In some embodiments, a conveyor can be used which includes a circular system where the biomass is conveyed multiple times through the various processes described above. In some other embodiments multiple treatment devices (e.g., electron beam generators) are used to treat the biomass multiple (e.g., 2, 3, 4 or more) times. In yet other embodiments, a single electron beam generator may be the source of multiple beams (e.g., 2, 3, 4 or more beams) that can be used for treatment of the biomass.

The effectiveness in changing the molecular/supermolecular structure and/or reducing the recalcitrance of the carbohydrate-containing biomass depends on the electron energy used and the dose applied, while exposure time depends on the power and dose. In some embodiments, the dose rate and total dose are adjusted so as not to destroy (e.g., char or burn) the biomass material. For example, the carbohydrates should not be damaged in the processing so that they can be released from the biomass intact, e.g. as monomeric sugars.

In some embodiments, the treatment (with any electron source or a combination of sources) is performed until the material receives a dose of at least about 0.05 Mrad, e.g., at least about 0.1, 0.25, 0.5, 0.75, 1.0, 2.5, 5.0, 7.5, 10.0, 15, 20, 25, 30, 40, 50, 60, 70, 80, 90, 100, 125, 150, 175, or 200 Mrad. In some embodiments, the treatment is performed until the material receives a dose of between 0.1-100 Mrad, 1-200, 5-200, 10-200, 5-150, 50-150 Mrad, 5-100, 5-50, 5-40, 10-50, 10-75, 15-50, 20-35 Mrad.

In some embodiments, relatively low doses of radiation are utilized, e.g., to increase the molecular weight of a cellulosic or lignocellulosic material (with any radiation source or a combination of sources described herein). For example, a dose of at least about 0.05 Mrad, e.g., at least about 0.1 Mrad or at least about 0.25, 0.5, 0.75, 1.0, 1.5, 2.0, 2.5, 3.0, 3.5, 4.0, or at least about 5.0 Mrad. In some embodiments, the irradiation is performed until the material receives a dose of between 0.1 Mrad and 2.0 Mrad, e.g., between 0.5 rad and 4.0 Mrad or between 1.0 Mrad and 3.0 Mrad.

It also can be desirable to irradiate from multiple directions, simultaneously or sequentially, in order to achieve a desired degree of penetration of radiation into the material. For example, depending on the density and moisture content of the material, such as wood, and the type of radiation source used (e.g., gamma or electron beam), the maximum penetration of radiation into the material may be only about 0.75 inch. In such cases, a thicker section (up to 1.5 inch) can be irradiated by first irradiating the material from one side, and then turning the material over and irradiating from the other side. Irradiation from multiple directions can be particularly useful with electron beam radiation, which irradiates faster than gamma radiation but typically does not achieve as great a penetration depth.

Radiation Opaque Materials

As previously discussed, the invention can include processing the material in a vault and/or bunker that is constructed using radiation opaque materials. In some implementations, the radiation opaque materials are selected to be capable of shielding the components from X-rays with high energy (short wavelength), which can penetrate many materials. One important factor in designing a radiation shielding enclosure is the attenuation length of the materials used, which will determine the required thickness for a particular material, blend of materials, or layered structure. The attenuation length is the penetration distance at which the radiation is reduced to approximately 1/e (e=Euler's number) times that of the incident radiation. Although virtually all materials are radiation opaque if thick enough, materials containing a high compositional percentage (e.g., density) of elements that have a high Z value (atomic number) have a shorter radiation attenuation length and thus if such materials are used a thinner, lighter shielding can be provided. Examples of high Z value materials that are used in radiation shielding are tantalum and lead. Another important parameter in radiation shielding is the halving distance, which is the thickness of a particular material that will reduce gamma ray intensity by 50%. As an example for X-ray radiation with an energy of 0.1 MeV the halving thickness is about 15.1 mm for concrete and about 2.7 mm for lead, while with an X-ray energy of 1 MeV the halving thickness for concrete is about 44.45 mm and for lead is about 7.9 mm. Radiation opaque materials can be materials that are thick or thin so long as they can reduce the radiation that passes through to the other side. Thus, if it is desired that a particular enclosure have a low wall thickness, e.g., for light weight or due to size constraints, the material chosen should have a sufficient Z value and/or attenuation length so that its halving length is less than or equal to the desired wall thickness of the enclosure.

In some cases, the radiation opaque material may be a layered material, for example having a layer of a higher Z value material, to provide good shielding, and a layer of a lower Z value material to provide other properties (e.g., structural integrity, impact resistance, etc.). In some cases, the layered material may be a "graded-Z" laminate, e.g., including a laminate in which the layers provide a gradient from high-Z through successively lower-Z elements. As previously described herein, in some cases the radiation opaque materials can be interlocking blocks, for example, lead and/or concrete blocks can be supplied by NELCO Worldwide (Burlington, Mass.), and re-configurable vaults can be utilized. For example, the blocks can include a dry-joint design so as to be reconfigurable and modular. For example, some materials that can be used include concrete blocks, MEGASHIELED™ MODULAR BLOCK, n-Series Lead Brick. For example, the radiation opaque materials can be high density materials e.g., having densities greater than about 100 lbs/cu ft, greater than about 200 lbs for cu ft or even greater than about 300 lb/cu ft. For example, NELCO (Burlington, Mass.) concrete blocks having about 147 lbs/cu ft, 250 lb/cu ft, 288 lb/cu ft and 300 lb/cu ft. The materials can be used to provide an entirely new construction or upgrade existing facilities.

A radiation opaque material can reduce the radiation passing through a structure (e.g., a wall, door, ceiling, enclosure, a series of these or combinations of these) formed of the material by about at least about 10%, (e.g., at least about 20%, at least about 30%, at least about 40%, at least about 50%, at least about 60%, at least about 70%, at least about 80%, at least about 90%, at least about 95%, at least about 96%, at least about 97%, at least about 98%, at least about 99%, at least about 99.9%, at least about 99.99%, at least about 99.999%) as compared to the incident radiation. Therefore, an enclosure made of a radiation opaque material can reduce the exposure of equipment/system/components by the same amount. Radiation opaque materials can include stainless steel, metals with Z values above 25 (e.g., lead, iron), concrete, dirt, sand and combinations thereof. Radiation opaque materials can include a barrier in the direction of the incident radiation of at least about 1 mm (e.g., 5 mm, 10 mm, 5 cm, 10 cm, 100 cm, 1 m and even at least 10 m).

Radiation Sources

The type of radiation determines the kinds of radiation sources used as well as the radiation devices and associated equipment. The methods, systems and equipment described herein, for example for treating materials with radiation, can utilized sources as described herein as well as any other useful source.

Sources of gamma rays include radioactive nuclei, such as isotopes of cobalt, calcium, technetium, chromium, gallium, indium, iodine, iron, krypton, samarium, selenium, sodium, thallium, and xenon.

Sources of X-rays include electron beam collision with metal targets, such as tungsten or molybdenum or alloys, or compact light sources, such as those produced commercially by Lyncean.

Alpha particles are identical to the nucleus of a helium atom and are produced by the alpha decay of various radioactive nuclei, such as isotopes of bismuth, polonium, astatine, radon, francium, radium, several actinides, such as actinium, thorium, uranium, neptunium, curium, californium, americium, and plutonium.

Sources for ultraviolet radiation include deuterium or cadmium lamps.

Sources for infrared radiation include sapphire, zinc, or selenide window ceramic lamps.

Sources for microwaves include klystrons, Slevin type RF sources, or atom beam sources that employ hydrogen, oxygen, or nitrogen gases.

Accelerators used to accelerate the particles (e.g., electrons or ions) can be DC (e.g., electrostatic DC or electrodynamic DC), RF linear, magnetic induction linear or continuous wave. For example, various irradiating devices may be used in the methods disclosed herein, including field ionization sources, electrostatic ion separators, field ionization generators, thermionic emission sources, microwave discharge ion sources, recirculating or static accelerators, dynamic linear accelerators, van de Graaff accelerators, Cockroft Walton accelerators (e.g., PELLETRON® accelerators), LINACS, Dynamitrons (e.g., DYNAMITRON® accelerators), cyclotrons, synchrotrons, betatrons, transformer-type accelerators, microtrons, plasma generators, cascade accelerators, and folded tandem accelerators. For example, cyclotron type accelerators are available from IBA, Belgium, such as the RHODOTRON™ system, while DC type accelerators are available from RDI, now IBA Industrial, such as the DYNAMITRON®. Other suitable accelerator systems include, for example: DC insulated core transformer (ICT) type systems, available from Nissin High Voltage, Japan; S-band LINACs, available from L3-PSD (USA), Linac Systems (France), Mevex (Canada), and Mitsubishi Heavy Industries (Japan); L-band LINACs, available from Iotron Industries (Canada); and ILU-based accelerators, available from Budker Laboratories (Russia). Ions and ion accelerators are discussed in Introductory Nuclear Physics, Kenneth S. Krane, John Wiley & Sons, Inc. (1988), Krsto Prelec, FIZTKA B 6 (1997) 4, 177-206, Chu, William T., "Overview of Light-Ion Beam Therapy", Columbus-Ohio, ICRU-IAEA Meeting, 18-20 Mar. 2006, Iwata, Y. et al., "Alternating-Phase-Focused IH-DTL for Heavy-Ion Medical Accelerators", Proceedings of EPAC 2006, Edinburgh, Scotland, and Leitner, C. M. et al., "Status of the Superconducting ECR Ion Source Venus", Proceedings of EPAC 2000, Vienna, Austria. Some particle accelerators and their uses are disclosed, for example, in U.S. Pat. No. 7,931,784 to Medoff, the complete disclosure of which is incorporated herein by reference.

Electrons may be produced by radioactive nuclei that undergo beta decay, such as isotopes of iodine, cesium, technetium, and iridium. Alternatively, an electron gun can be used as an electron source via thermionic emission and accelerated through an accelerating potential. An electron gun generates electrons, which are then accelerated through a large potential (e.g., greater than about 500 thousand, greater than about 1 million, greater than about 2 million, greater than about 5 million, greater than about 6 million, greater than about 7 million, greater than about 8 million, greater than about 9 million, or even greater than 10 million volts) and then scanned magnetically in the x-y plane, where the electrons are initially accelerated in the z direction down the accelerator tube and extracted through a foil window. Scanning the electron beams is useful for increasing the irradiation surface when irradiating materials, e.g., a biomass, that is conveyed through the scanned beam. Scanning the electron beam also distributes the thermal load homogenously on the window and helps reduce the foil window rupture due to local heating by the electron beam. Window foil rupture is a cause of significant down-time due to subsequent necessary repairs and re-starting the electron gun.

Various other irradiating devices may be used in the methods disclosed herein, including field ionization sources, electrostatic ion separators, field ionization generators, thermionic emission sources, microwave discharge ion sources, recirculating or static accelerators, dynamic linear accelerators, van de Graaff accelerators, and folded tandem accelerators. Such devices are disclosed, for example, in U.S. Pat. No. 7,931,784 to Medoff, the complete disclosure of which is incorporated herein by reference.

A beam of electrons can be used as the radiation source. A beam of electrons has the advantages of high dose rates (e.g., 1, 5, or even 10 Mrad per second), high throughput, less containment, and less confinement equipment. Electron beams can also have high electrical efficiency (e.g., 80%), allowing for lower energy usage relative to other radiation methods, which can translate into a lower cost of operation and lower greenhouse gas emissions corresponding to the smaller amount of energy used. Electron beams can be generated, e.g., by electrostatic generators, cascade generators, transformer generators, low energy accelerators with a scanning system, low energy accelerators with a linear cathode, linear accelerators, and pulsed accelerators.

Electrons can also be more efficient at causing changes in the molecular structure of carbohydrate-containing materials, for example, by the mechanism of chain scission. In addition, electrons having energies of 0.5-10 MeV can penetrate low density materials, such as the biomass materials described herein, e.g., materials having a bulk density of less than 0.5 g/cm$^3$, and a depth of 0.3-10 cm. Electrons as an ionizing radiation source can be useful, e.g., for relatively thin piles, layers or beds of materials, e.g., less than about 0.5 inch, e.g., less than about 0.4 inch, 0.3 inch, 0.25 inch, or less than about 0.1 inch. In some embodiments, the energy of each electron of the electron beam is from about 0.3 MeV to about 2.0 MeV (million electron volts), e.g., from about 0.5 MeV to about 1.5 MeV, or from about 0.7 MeV to about 1.25 MeV. Methods of irradiating materials are discussed in U.S. Pat. App. Pub. 2012/0100577 A1, filed Oct. 18, 2011, the entire disclosure of which is herein incorporated by reference.

Electron beam irradiation devices may be procured commercially or built. For example elements or components such inductors, capacitors, casings, power sources, cables, wiring, voltage control systems, current control elements, insulating material, microcontrollers and cooling equipment can be purchased and assembled into a device. Optionally, a commercial device can be modified and/or adapted. For example, devices and components can be purchased from any of the commercial sources described herein including Ion Beam Applications (Louvain-la-Neuve, Belgium), Wasik Associates Inc. (Dracut, Mass.), NHV Corporation (Japan), the Titan Corporation (San Diego, Calif.), Vivirad High Voltage Corp (Billerica, Mass.) and/or Budker Laboratories (Russia). Typical electron energies can be 0.5 MeV, 1 MeV, 2 MeV, 4.5 MeV, 7.5 MeV, or 10 MeV. Typical electron beam irradiation device power can be 1 kW, 5 kW, 10 kW, 20 kW, 50 kW, 60 kW, 70 kW, 80 kW, 90 kW, 100 kW, 125 kW, 150 kW, 175 kW, 200 kW, 250 kW, 300 kW, 350 kW, 400 kW, 450 kW, 500 kW, 600 kW, 700 kW, 800 kW, 900 kW or even 1000 kW. Accelerators that can be used include NHV irradiators medium energy series EPS-500 (e.g., 500 kV accelerator voltage and 65, 100 or 150 mA beam current), EPS-800 (e.g., 800 kV accelerator voltage and 65 or 100 mA beam current), or EPS-1000 (e.g., 1000 kV accelerator voltage and 65 or 100 mA beam current). Also, accelerators from NHV's high energy series can be used such as EPS-1500 (e.g., 1500 kV accelerator voltage and 65 mA beam current), EPS-2000 (e.g., 2000 kV accelerator voltage and 50 mA beam current), EPS-3000 (e.g., 3000 kV accelerator voltage and 50 mA beam current) and EPS-5000 (e.g., 5000 and 30 mA beam current).

Tradeoffs in considering electron beam irradiation device power specifications include cost to operate, capital costs, depreciation, and device footprint. Tradeoffs in considering exposure dose levels of electron beam irradiation would be energy costs and environment, safety, and health (ESH) concerns. Typically, generators are housed in a vault, e.g., of lead or concrete, especially for production from X-rays that are generated in the process. Tradeoffs in considering electron energies include energy costs.

The electron beam irradiation device can produce either a fixed beam or a scanning beam. A scanning beam may be advantageous with large scan sweep length and high scan speeds, as this would effectively replace a large, fixed beam width. Further, available sweep widths of 0.5 m, 1 m, 2 m or more are available. The scanning beam is preferred in most embodiments described herein because of the larger scan width and reduced possibility of local heating and failure of the windows.

Electron Guns—Windows

The extraction system for an electron accelerator can include two window foils. The cooling gas in the two foil window extraction system can be a purge gas or a mixture, for example air, or a pure gas. In one embodiment the gas is an inert gas such as nitrogen, argon, helium and or carbon dioxide. It is preferred to use a gas rather than a liquid since energy losses to the electron beam are minimized. Mixtures of pure gas can also be used, either pre-mixed or mixed in line prior to impinging on the windows or in the space between the windows. The cooling gas can be cooled, for example, by using a heat exchange system (e.g., a chiller)

and/or by using boil off from a condensed gas (e.g., liquid nitrogen, liquid helium). Window foils are described in PCT/US2013/64332 filed Oct. 10, 2013 the full disclosure of which is incorporated by reference herein.

Heating and Throughput During Radiation Treatment

Several processes can occur in biomass when electrons from an electron beam interact with matter in inelastic collisions. For example, ionization of the material, chain scission of polymers in the material, cross linking of polymers in the material, oxidation of the material, generation of X-rays ("Bremsstrahlung") and vibrational excitation of molecules (e.g., phonon generation). Without being bound to a particular mechanism, the reduction in recalcitrance can be due to several of these inelastic collision effects, for example ionization, chain scission of polymers, oxidation and phonon generation. Some of the effects (e.g., especially X-ray generation), necessitate shielding and engineering barriers, for example, enclosing the irradiation processes in a concrete (or other radiation opaque material) vault. Another effect of irradiation, vibrational excitation, is equivalent to heating up the sample. Heating the sample by irradiation can help in recalcitrance reduction, but excessive heating can destroy the material, as will be explained below.

The adiabatic temperature rise (ΔT) from adsorption of ionizing radiation is given by the equation: $\Delta T = D/C_p$: where D is the average dose in kGy, Cp is the heat capacity in J/g °C., and ΔT is the change in temperature in °C. A typical dry biomass material will have a heat capacity close to 2. Wet biomass will have a higher heat capacity dependent on the amount of water since the heat capacity of water is very high (4.19 J/g °C.). Metals have much lower heat capacities, for example 304 stainless steel has a heat capacity of 0.5 J/g °C. The temperature change due to the instant adsorption of radiation in a biomass and stainless steel for various doses of radiation is shown in Table 1. At the higher temperatures biomass will decompose causing extreme deviation from the estimated changes in temperature.

TABLE 1

Calculated Temperature increase for biomass and stainless steel.

| Dose (Mrad) | Estimated Biomass ΔT (° C.) | Steel ΔT (° C.) |
| --- | --- | --- |
| 10 | 50 | 200 |
| 50 | 250 (decomposed) | 1000 |
| 100 | 500 (decomposed) | 2000 |
| 150 | 750 (decomposed) | 3000 |
| 200 | 1000 (decomposed) | 4000 |

High temperatures can destroy and or modify the biopolymers in biomass so that the polymers (e.g., cellulose) are unsuitable for further processing. A biomass subjected to high temperatures can become dark, sticky and give off odors indicating decomposition. The stickiness can even make the material hard to convey. The odors can be unpleasant and be a safety issue. In fact, keeping the biomass below about 200° C. has been found to be beneficial in the processes described herein (e.g., below about 190° C., below about 180° C., below about 170° C., below about 160° C., below about 150° C., below about 140° C., below about 130° C., below about 120° C., below about 110° C., between about 60° C. and 180° C., between about 60° C. and 160° C., between about 60° C. and 150° C., between about 60° C. and 140° C., between about 60° C. and 130° C., between about 60° C. and 120° C., between about 80° C. and 180° C., between about 100° C. and 180° C., between about 120° C. and 180° C., between about 140° C. and 180° C., between about 160° C. and 180° C., between about 100° C. and 140° C., between about 80° C. and 120° C.).

It has been found that irradiation above about 10 Mrad is desirable for the processes described herein (e.g., reduction of recalcitrance). A high throughput is also desirable so that the irradiation does not become a bottle neck in processing the biomass. The treatment is governed by a Dose rate equation: M=FP/D time, where M is the mass of irradiated material (kg), F is the fraction of power that is adsorbed (unit less), P is the emitted power (kW=Voltage in MeV×Current in mA), time is the treatment time (sec) and D is the adsorbed dose (kGy). In an exemplary process where the fraction of adsorbed power is fixed, the Power emitted is constant and a set dosage is desired, the throughput (e.g., M, the biomass processed) can be increased by increasing the irradiation time. However, increasing the irradiation time without allowing the material to cool, can excessively heat the material as exemplified by the calculations shown above. Since biomass has a low thermal conductivity (less than about 0.1 $Wm^{-1}K^{-1}$), heat dissipation is slow, unlike, for example metals (greater than about 10 $Wm^{-1}K^{-1}$) which can dissipate energy quickly as long as there is a heat sink to transfer the energy to.

Electron Guns—Beam Stops

In some embodiments the systems and methods include a beam stop (e.g., a shutter). For example, the beam stop can be used to quickly stop or reduce the irradiation of material without powering down the electron beam device. Alternatively the beam stop can be used while powering up the electron beam, e.g., the beam stop can stop the electron beam until a beam current of a desired level is achieved. The beam stop can be placed between the primary foil window and a secondary foil window. For example the beam stop can be mounted so that it is movable, that is, so that it can be moved into and out of the beam path. Even partial coverage of the beam can be used, for example, to control the dose of irradiation. The beam stop can be mounted to the floor, to a conveyor for the biomass, to a wall, to the radiation device (e.g., at the scan horn), or to any structural support. Preferably the beam stop is fixed in relation to the scan horn so that the beam can be effectively controlled by the beam stop. The beam stop can incorporate a hinge, a rail, wheels, slots, or other means allowing for its operation in moving into and out of the beam. The beam stop can be made of any material that will stop at least 5% of the electrons, e.g., at least 10%, 20%, 30%, 40%, 50%, 60%, 70%, at least 80%, 85%, 90%, 91%, 92%, 93%, 94%, 95%, 96%, 97%, 98%, 99% or even about 100% of the electrons.

The beam stop can be made of a metal including, but not limited to, stainless steel, lead, iron, molybdenum, silver, gold, titanium, aluminum, tin, or alloys of these, or laminates (layered materials) made with such metals (e.g., metal-coated ceramic, metal-coated polymer, metal-coated composite, multilayered metal materials).

The beam stop can be cooled, for example, with a cooling fluid such as an aqueous solution or a gas. The beam stop can be partially or completely hollow, for example with cavities. Interior spaces of the beam stop can be used for cooling fluids and gases. The beam stop can be of any shape, including flat, curved, round, oval, square, rectangular, beveled and wedged shapes.

The beam stop can have perforations so as to allow some electrons through, thus controlling (e.g., reducing) the levels of radiation across the whole area of the window, or in specific regions of the window. The beam stop can be a mesh formed, for example, from fibers or wires. Multiple beam stops can be used, together or independently, to control the irradiation. The beam stop can be remotely controlled, e.g., by radio signal or hard wired to a motor for moving the beam into or out of position.

Beam Dumps

The embodiments disclosed herein can also include a beam dump when utilizing a radiation treatment. A beam dump's purpose is to safely absorb a beam of charged particles. Like a beam stop, a beam dump can be used to block the beam of charged particles. However, a beam dump is much more robust than a beam stop, and is intended to block the full power of the electron beam for an extended period of time. They are often used to block the beam as the accelerator is powering up.

Beam dumps are also designed to accommodate the heat generated by such beams, and are usually made from materials such as copper, aluminum, carbon, beryllium, tungsten, or mercury. Beam dumps can be cooled, for example, using a cooling fluid that can be in thermal contact with the beam dump.

Biomass Materials

Lignocellulosic materials include, but are not limited to, wood, particle board, forestry wastes (e.g., sawdust, aspen wood, wood chips), grasses, (e.g., switchgrass, miscanthus, cord grass, reed canary grass), grain residues, (e.g., rice hulls, oat hulls, wheat chaff, barley hulls), agricultural waste (e.g., silage, canola straw, wheat straw, barley straw, oat straw, rice straw, jute, hemp, flax, bamboo, sisal, abaca, corn cobs, corn stover, soybean stover, corn fiber, alfalfa, hay, coconut hair), sugar processing residues (e.g., bagasse, beet pulp, agave bagasse), algae, seaweed, manure, sewage, and mixtures of any of these.

In some cases, the lignocellulosic material includes corncobs. Ground or hammermilled corncobs can be spread in a layer of relatively uniform thickness for irradiation, and after irradiation are easy to disperse in the medium for further processing. To facilitate harvest and collection, in some cases the entire corn plant is used, including the corn stalk, corn kernels, and in some cases even the root system of the plant.

Advantageously, no additional nutrients (other than a nitrogen source, e.g., urea or ammonia) are required during fermentation of corncobs or cellulosic or lignocellulosic materials containing significant amounts of corncobs.

Corncobs, before and after comminution, are also easier to convey and disperse, and have a lesser tendency to form explosive mixtures in air than other cellulosic or lignocellulosic materials such as hay and grasses.

Cellulosic materials include, for example, paper, paper products, paper waste, paper pulp, pigmented papers, loaded papers, coated papers, filled papers, magazines, printed matter (e.g., books, catalogs, manuals, labels, calendars, greeting cards, brochures, prospectuses, newsprint), printer paper, polycoated paper, card stock, cardboard, paperboard, materials having a high α-cellulose content such as cotton, and mixtures of any of these. For example paper products as described in U.S. application Ser. No. 13/396,365 ("Magazine Feedstocks" by Medoff et al., filed Feb. 14, 2012), the full disclosure of which is incorporated herein by reference.

Cellulosic materials can also include lignocellulosic materials which have been partially or fully de-lignified.

In some instances other biomass materials can be utilized, for example starchy materials. Starchy materials include starch itself, e.g., corn starch, wheat starch, potato starch or rice starch, a derivative of starch, or a material that includes starch, such as an edible food product or a crop. For example, the starchy material can be arracacha, buckwheat, banana, barley, cassava, kudzu, oca, sago, sorghum, regular household potatoes, sweet potato, taro, yams, or one or more beans, such as favas, lentils or peas. Blends of any two or more starchy materials are also starchy materials. Mixtures of starchy, cellulosic and or lignocellulosic materials can also be used. For example, a biomass can be an entire plant, a part of a plant or different parts of a plant, e.g., a wheat plant, cotton plant, a corn plant, rice plant or a tree. The starchy materials can be treated by any of the methods described herein.

Microbial materials that can be used as feedstock can include, but are not limited to, any naturally occurring or genetically modified microorganism or organism that contains or is capable of providing a source of carbohydrates (e.g., cellulose), for example, protists, e.g., animal protists (e.g., protozoa such as flagellates, amoeboids, ciliates, and sporozoa) and plant protists (e.g., algae such alveolates, chlorarachniophytes, cryptomonads, euglenids, glaucophytes, haptophytes, red algae, stramenopiles, and viridaeplantae). Other examples include seaweed, plankton (e.g., macroplankton, mesoplankton, microplankton, nanoplankton, picoplankton, and femptoplankton), phytoplankton, bacteria (e.g., gram positive bacteria, gram negative bacteria, and extremophiles), yeast and/or mixtures of these. In some instances, microbial biomass can be obtained from natural sources, e.g., the ocean, lakes, bodies of water, e.g., salt water or fresh water, or on land. Alternatively or in addition, microbial biomass can be obtained from culture systems, e.g., large scale dry and wet culture and fermentation systems. In other embodiments, the biomass materials, such as cellulosic, starchy and lignocellulosic feedstock materials, can be obtained from transgenic microorganisms and plants that have been modified with respect to a wild type variety. Such modifications may be, for example, through the iterative steps of selection and breeding to obtain desired traits in a plant. Furthermore, the plants can have had genetic material removed, modified, silenced and/or added with respect to the wild type variety. For example, genetically modified plants can be produced by recombinant DNA methods, where genetic modifications include introducing or modifying specific genes from parental varieties, or, for example, by using transgenic breeding wherein a specific gene or genes are introduced to a plant from a different species of plant and/or bacteria. Another way to create genetic variation is through mutation breeding wherein new alleles are artificially created from endogenous genes. The artificial genes can be created by a variety of ways including treating the plant or seeds with, for example, chemical mutagens (e.g., using alkylating agents, epoxides, alkaloids, peroxides, formaldehyde), irradiation (e.g., X-rays, gamma rays, neutrons, beta particles, alpha particles, protons, deuterons, UV radiation) and temperature shocking or other external stressing and subsequent selection techniques. Other methods of providing modified genes is through error prone PCR and DNA shuffling followed by insertion of the desired modified DNA into the desired plant or seed. Methods of introducing the desired genetic variation in the seed or plant include, for example, the use of a bacterial carrier, biolistics, calcium phosphate precipitation, electroporation, gene splicing, gene silencing, lipofection, microinjection and viral carriers. Additional genetically modified materials have been described in U.S. application Ser. No. 13/396,369 filed Feb. 14, 2012, the full disclosure of which is incorporated herein by reference. Any of the methods described herein can be practiced with mixtures of any biomass materials described herein.

Other Materials

Other materials (e.g., natural or synthetic materials), for example polymers, can be treated and/or made utilizing the methods, equipment and systems described herein. For example polyethylene (e.g., linear low density ethylene and high density polyethylene), polystyrenes, sulfonated polystyrenes, poly (vinyl chloride), polyesters (e.g., nylons, DACRON™, KODEL™), polyalkylene esters, poly vinyl esters, polyamides (e.g., KEVLAR™), polyethylene terephthalate, cellulose acetate, acetal, poly acrylonitrile, polycarbonates(LEXAN™), acrylics [e.g., poly (methyl methacrylate), poly(methyl methacrylate), polyacrylonitrile], Poly urethanes, polypropylene, poly butadiene, polyisobutylene, polyacrylonitrile, polychloroprene (e.g. neoprene), poly(cis-1,4-isoprene) [e.g., natural rubber], poly (trans-1,4-isoprene) [e.g., gutta percha], phenol formaldehyde, melamine formaldehyde, epoxides, polyesters, poly amines, polycarboxylic acids, polylactic acids, polyvinyl alcohols, polyanhydrides, poly fluoro carbons (e.g., TEFLON™), silicons (e.g., silicone rubber), polysilanes, poly ethers (e.g., polyethylene oxide, polypropylene oxide), waxes, oils and mixtures of these. Also included are plastics, rubbers, elastomers, fibers, waxes, gels, oils, adhesives, thermoplastics, thermosets, biodegradable polymers, resins made with these polymers, other polymers, other materials and combinations thereof. The polymers can be made by any useful method including cationic polymerization, anionic polymerization, radical polymerization, metathesis polymerization, ring opening polymerization, graft polymerization, addition polymerization. In some cases the treatments disclosed herein can be used, for example, for radically initiated graft polymerization and cross linking. Composites of polymers, for example with glass, metals, biomass (e.g., fibers, particles), ceramics can also be treated and/or made.

Other materials that can be treated by using the methods, systems and equipment disclosed herein are ceramic materials, minerals, metals, inorganic compounds. For example, silicon and germanium crystals, silicon nitrides, metal oxides, semiconductors, insulators, cements and or conductors.

In addition, manufactured multipart or shaped materials (e.g., molded, extruded, welded, riveted, layered or combined in any way) can be treated, for example cables, pipes, boards, enclosures, integrated semiconductor chips, circuit boards, wires, tires, windows, laminated materials, gears, belts, machines, combinations of these. For example, treating a material by the methods described herein can modify the surfaces, for example, making them susceptible to further functionalization, combinations (e.g., welding) and/or treatment can cross link the materials.

Biomass Material Preparation—Mechanical Treatments

The biomass can be in a dry form, for example with less than about 35% moisture content (e.g., less than about 20%, less than about 15%, less than about 10% less than about 5%, less than about 4%, less than about 3%, less than about 2% or even less than about 1%). The biomass can also be delivered in a wet state, for example as a wet solid, a slurry or a suspension with at least about 10 wt. % solids (e.g., at least about 20 wt. %, at least about 30 wt. %, at least about 40 wt. %, at least about 50 wt. %, at least about 60 wt. %, at least about 70 wt. %).

The processes disclosed herein can utilize low bulk density materials, for example cellulosic or lignocellulosic feedstocks that have been physically pretreated to have a bulk density of less than about 0.75 g/cm$^3$, e.g., less than about 0.7, 0.65, 0.60, 0.50, 0.35, 0.25, 0.20, 0.15, 0.10, 0.05 or less, e.g., less than about 0.025 g/cm$^3$. Bulk density is determined using ASTM D1895B. Briefly, the method involves filling a measuring cylinder of known volume with a sample and obtaining a weight of the sample. The bulk density is calculated by dividing the weight of the sample in grams by the known volume of the cylinder in cubic centimeters. If desired, low bulk density materials can be densified, for example, by methods described in U.S. Pat. No. 7,971,809 to Medoff, the full disclosure of which is hereby incorporated by reference.

In some cases, the pre-treatment processing includes screening of the biomass material. Screening can be through a mesh or perforated plate with a desired opening size, for example, less than about 6.35 mm (¼ inch, 0.25 inch), (e.g., less than about 3.18 mm (⅛ inch, 0.125 inch), less than about 1.59 mm (1/16 inch, 0.0625 inch), is less than about 0.79 mm (1/32 inch, 0.03125 inch), e.g., less than about 0.51 mm (1/50 inch, 0.02000 inch), less than about 0.40 mm (1/64 inch, 0.015625 inch), less than about 0.23 mm (0.009 inch), less than about 0.20 mm (1/128 inch, 0.0078125 inch), less than about 0.18 mm (0.007 inch), less than about 0.13 mm (0.005 inch), or even less than about 0.10 mm (1/256 inch, 0.00390625 inch)). In one configuration the desired biomass falls through the perforations or screen and thus biomass larger than the perforations or screen are not irradiated. These larger materials can be re-processed, for example by comminuting, or they can simply be removed from processing. In another configuration material that is larger than the perforations is irradiated and the smaller material is removed by the screening process or recycled. In this kind of a configuration, the conveyor itself (for example a part of the conveyor) can be perforated or made with a mesh. For example, in one particular embodiment the biomass material may be wet and the perforations or mesh allow water to drain away from the biomass before irradiation.

Screening of material can also be by a manual method, for example by an operator or mechanoid (e.g., a robot equipped with a color, reflectivity or other sensor) that removes unwanted material. Screening can also be by magnetic screening wherein a magnet is disposed near the conveyed material and the magnetic material is removed magnetically.

Optional pre-treatment processing can include heating the material. For example a portion of a conveyor conveying the material or other material can be sent through a heated zone. The heated zone can be created, for example, by IR radiation, microwaves, combustion (e.g., gas, coal, oil, biomass), resistive heating and/or inductive coils. The heat can be applied from at least one side or more than one side, can be continuous or periodic and can be for only a portion of the material or all the material. For example, a portion of the conveying trough can be heated by use of a heating jacket. Heating can be, for example, for the purpose of drying the material. In the case of drying the material, this can also be facilitated, with or without heating, by the movement of a gas (e.g., air, oxygen, nitrogen, He, CO$_2$, Argon) over and/or through the biomass as it is being conveyed.

Optionally, pre-treatment processing can include cooling the material. Cooling material is described in U.S. Pat. No. 7,900,857 to Medoff, the disclosure of which in incorporated herein by reference. For example, cooling can be by supplying a cooling fluid, for example water (e.g., with glycerol), or nitrogen (e.g., liquid nitrogen) to the bottom of the conveying trough. Alternatively, a cooling gas, for example, chilled nitrogen can be blown over the biomass materials or under the conveying system.

Another optional pre-treatment processing method can include adding a material to the biomass or other feedstocks. The additional material can be added by, for example, by showering, sprinkling and or pouring the material onto the biomass as it is conveyed. Materials that can be added include, for example, metals, ceramics and/or ions as described in U.S. Pat. App. Pub. 2010/0105119 A1 (filed Oct. 26, 2009) and U.S. Pat. App. Pub. 2010/0159569 A1 (filed Dec. 16, 2009), the entire disclosures of which are incorporated herein by reference. Optional materials that can be added include acids and bases. Other materials that can be added are oxidants (e.g., peroxides, chlorates), polymers, polymerizable monomers (e.g., containing unsaturated bonds), water, catalysts, enzymes and/or organisms. Materials can be added, for example, in pure form, as a solution in a solvent (e.g., water or an organic solvent) and/or as a solution. In some cases the solvent is volatile and can be made to evaporate e.g., by heating and/or blowing gas as previously described. The added material may form a uniform coating on the biomass or be a homogeneous mixture of different components (e.g., biomass and additional material). The added material can modulate the subsequent irradiation step by increasing the efficiency of the irradiation, damping the irradiation or changing the effect of the irradiation (e.g., from electron beams to X-rays or heat). The method may have no impact on the irradiation but may be useful for further downstream processing. The added material may help in conveying the material, for example, by lowering dust levels.

Biomass can be delivered to a conveyor (e.g., vibratory conveyors used in the vaults herein described) by a belt conveyor, a pneumatic conveyor, a screw conveyor, a hopper, a pipe, manually or by a combination of these. The biomass can, for example, be dropped, poured and/or placed onto the conveyor by any of these methods. In some embodiments the material is delivered to the conveyor using an enclosed material distribution system to help maintain a low oxygen atmosphere and/or control dust and fines. Lofted or air suspended biomass fines and dust are undesirable because these can form an explosion hazard or damage the window foils of an electron gun (if such a device is used for treating the material).

The material can be leveled to form a uniform thickness between about 0.0312 and 5 inches (e.g., between about 0.0625 and 2.000 inches, between about 0.125 and 1 inches, between about 0.125 and 0.5 inches, between about 0.3 and 0.9 inches, between about 0.2 and 0.5 inches between about 0.25 and 1.0 inches, between about 0.25 and 0.5 inches, 0.100+/−0.025 inches, 0.150+/−0.025 inches, 0.200+/−0.025 inches, 0.250+/−0.025 inches, 0.300+/−0.025 inches, 0.350+/−0.025 inches, 0.400+/−0.025 inches, 0.450+/−0.025 inches, 0.500+/−0.025 inches, 0.550+/−0.025 inches, 0.600+/−0.025 inches, 0.700+/−0.025 inches, 0.750+/−0.025 inches, 0.800+/−0.025 inches, 0.850+/−0.025 inches, 0.900+/−0.025 inches, 0.900+/−0.025 inches.

Generally, it is preferred to convey the material as quickly as possible through the electron beam to maximize throughput. For example, the material can be conveyed at rates of at least 1 ft/min, e.g., at least 2 ft/min, at least 3 ft/min, at least 4 ft/min, at least 5 ft/min, at least 10 ft/min, at least 15 ft/min, 20, 25, 30, 35, 40, 45, 50 ft/min. The rate of conveying is related to the beam current, for example, for a ¼ inch thick biomass and 100 mA, the conveyor can move at about 20 ft/min to provide a useful irradiation dosage, at 50 mA the conveyor can move at about 10 ft/min to provide approximately the same irradiation dosage.

After the biomass material has been conveyed through the radiation zone, optional post-treatment processing can be done. The optional post-treatment processing can, for example, be a process described with respect to the pre-irradiation processing. For example, the biomass can be screened, heated, cooled, and/or combined with additives. Uniquely to post-irradiation, quenching of the radicals can occur, for example, quenching of radicals by the addition of fluids or gases (e.g., oxygen, nitrous oxide, ammonia, liquids), using pressure, heat, and/or the addition of radical scavengers. For example, the biomass can be conveyed out of the enclosed conveyor and exposed to a gas (e.g., oxygen) where it is quenched, forming carboxylated groups. In one embodiment the biomass is exposed during irradiation to the reactive gas or fluid. Quenching of biomass that has been irradiated is described in U.S. Pat. No. 8,083,906 to Medoff, the entire disclosure of which is incorporate herein by reference.

If desired, one or more mechanical treatments can be used in addition to irradiation to further reduce the recalcitrance of the carbohydrate-containing material. These processes can be applied before, during and or after irradiation.

In some cases, the mechanical treatment may include an initial preparation of the feedstock as received, e.g., size reduction of materials, such as by comminution, e.g., cutting, grinding, shearing, pulverizing or chopping. For example, in some cases, loose feedstock (e.g., recycled paper, starchy materials, or switchgrass) is prepared by shearing or shredding. Mechanical treatment may reduce the bulk density of the carbohydrate-containing material, increase the surface area of the carbohydrate-containing material and/or decrease one or more dimensions of the carbohydrate-containing material.

Alternatively, or in addition, the feedstock material can be treated with another treatment, for example chemical treatments, such as with an acid (HCl, H$_2$SO$_4$, H$_3$PO$_4$), a base (e.g., KOH and NaOH), a chemical oxidant (e.g., peroxides, chlorates, ozone), irradiation, steam explosion, pyrolysis, sonication, oxidation, chemical treatment. The treatments can be in any order and in any sequence and combinations. For example, the feedstock material can first be physically treated by one or more treatment methods, e.g., chemical treatment including and in combination with acid hydrolysis (e.g., utilizing HCl, H$_2$SO$_4$, H$_3$PO$_4$), radiation, sonication, oxidation, pyrolysis or steam explosion, and then mechanically treated. This sequence can be advantageous since materials treated by one or more of the other treatments, e.g., irradiation or pyrolysis, tend to be more brittle and, therefore, it may be easier to further change the structure of the material by mechanical treatment. As another example, a feedstock material can be conveyed through ionizing radiation using a conveyor as described herein and then mechanically treated. Chemical treatment can remove some or all of the lignin (for example, chemical pulping) and can partially or completely hydrolyze the material. The methods also can be used with pre-hydrolyzed material. The methods also can be used with material that has not been pre hydrolyzed The methods can be used with mixtures of hydrolyzed and non-hydrolyzed materials, for example with about 50% or more non-hydrolyzed material, with about 60% or more non-hydrolyzed material, with about 70% or more non-hydrolyzed material, with about 80% or more non-hydrolyzed material or even with 90% or more non-hydrolyzed material.

In addition to size reduction, which can be performed initially and/or later in processing, mechanical treatment can also be advantageous for "opening up," "stressing," breaking or shattering the carbohydrate-containing materials, making the cellulose of the materials more susceptible to chain scission and/or disruption of crystalline structure during the physical treatment.

Methods of mechanically treating the carbohydrate-containing material include, for example, milling or grinding. Milling may be performed using, for example, a hammer mill, ball mill, colloid mill, conical or cone mill, disk mill, edge mill, Wiley mill, grist mill or other mill. Grinding may be performed using, for example, a cutting/impact type grinder. Some exemplary grinders include stone grinders, pin grinders, coffee grinders, and burr grinders. Grinding or milling may be provided, for example, by a reciprocating pin or other element, as is the case in a pin mill. Other mechanical treatment methods include mechanical ripping or tearing, other methods that apply pressure to the fibers, and air attrition milling. Suitable mechanical treatments further include any other technique that continues the disruption of the internal structure of the material that was initiated by the previous processing steps.

Mechanical feed preparation systems can be configured to produce streams with specific characteristics such as, for example, specific maximum sizes, specific length-to-width, or specific surface areas ratios. Physical preparation can increase the rate of reactions, improve the movement of material on a conveyor, improve the irradiation profile of the material, improve the radiation uniformity of the material, or reduce the processing time required by opening up the materials and making them more accessible to processes and/or reagents, such as reagents in a solution.

The bulk density of feedstocks can be controlled (e.g., increased). In some situations, it can be desirable to prepare a low bulk density material, e.g., by densifying the material (e.g., densification can make it easier and less costly to transport to another site) and then reverting the material to a lower bulk density state (e.g., after transport). The material can be densified, for example from less than about 0.2 g/cc to more than about 0.9 g/cc (e.g., less than about 0.3 to more than about 0.5 g/cc, less than about 0.3 to more than about 0.9 g/cc, less than about 0.5 to more than about 0.9 g/cc, less than about 0.3 to more than about 0.8 g/cc, less than about 0.2 to more than about 0.5 g/cc). For example, the material can be densified by the methods and equipment disclosed in U.S. Pat. No. 7,932,065 to Medoff and International Publication No. WO 2008/073186 (which was filed Oct. 26, 2007, was published in English, and which designated the United States), the full disclosures of which are incorporated herein by reference. Densified materials can be processed by any of the methods described herein, or any material processed by any of the methods described herein can be subsequently densified.

In some embodiments, the material to be processed is in the form of a fibrous material that includes fibers provided by shearing a fiber source. For example, the shearing can be performed with a rotary knife cutter.

For example, a fiber source, e.g., that is recalcitrant or that has had its recalcitrance level reduced, can be sheared, e.g., in a rotary knife cutter, to provide a first fibrous material. The first fibrous material is passed through a first screen, e.g., having an average opening size of 1.59 mm or less (1/16 inch, 0.0625 inch), provide a second fibrous material. If desired, the fiber source can be cut prior to the shearing, e.g., with a shredder. For example, when a paper is used as the fiber source, the paper can be first cut into strips that are, e.g., ¼- to ½-inch wide, using a shredder, e.g., a counter-rotating screw shredder, such as those manufactured by Munson (Utica, N.Y.). As an alternative to shredding, the paper can be reduced in size by cutting to a desired size using a guillotine cutter. For example, the guillotine cutter can be used to cut the paper into sheets that are, e.g., 10 inches wide by 12 inches long.

In some embodiments, the shearing of the fiber source and the passing of the resulting first fibrous material through a first screen are performed concurrently. The shearing and the passing can also be performed in a batch-type process.

For example, a rotary knife cutter can be used to concurrently shear the fiber source and screen the first fibrous material. A rotary knife cutter includes a hopper that can be loaded with a shredded fiber source prepared by shredding a fiber source.

In some implementations, the feedstock is physically treated prior to saccharification and/or fermentation. Physical treatment processes can include one or more of any of those described herein, such as mechanical treatment, chemical treatment, irradiation, sonication, oxidation, pyrolysis or steam explosion. Treatment methods can be used in combinations of two, three, four, or even all of these technologies (in any order). When more than one treatment method is used, the methods can be applied at the same time or at different times. Other processes that change a molecular structure of a biomass feedstock may also be used, alone or in combination with the processes disclosed herein.

Mechanical treatments that may be used, and the characteristics of the mechanically treated carbohydrate-containing materials, are described in further detail in U.S. Pat. App. Pub. 2012/0100577 A1, filed Oct. 18, 2011, the full disclosure of which is hereby incorporated herein by reference.

Sonication, Pyrolysis, Oxidation, Steam Explosion

If desired, one or more sonication, pyrolysis, oxidative, or steam explosion processes can be used instead of or in addition to irradiation to reduce or further reduce the recalcitrance of the carbohydrate-containing material. For example, these processes can be applied before, during and or after irradiation. These processes are described in detail in U.S. Pat. No. 7,932,065 to Medoff, the full disclosure of which is incorporated herein by reference.

Intermediates and Products

Using the processes described herein, the biomass material can be converted to one or more products, such as energy, fuels, foods and materials. For example, intermediates and products such as organic acids, salts of organic acids, anhydrides, esters of organic acids and fuels, e.g., fuels for internal combustion engines or feedstocks for fuel cells. Systems and processes are described herein that can use as feedstock cellulosic and/or lignocellulosic materials that are readily available, but often can be difficult to process, e.g., municipal waste streams and waste paper streams, such as streams that include newspaper, Kraft paper, corrugated paper or mixtures of these.

Specific examples of products include, but are not limited to, hydrogen, sugars (e.g., glucose, xylose, arabinose, mannose, galactose, fructose, disaccharides, oligosaccharides and polysaccharides), alcohols (e.g., monohydric alcohols or dihydric alcohols, such as ethanol, n-propanol, isobutanol, sec-butanol, tert-butanol or n-butanol), hydrated or hydrous alcohols (e.g., containing greater than 10%, 20%, 30% or even greater than 40% water), biodiesel, organic acids, hydrocarbons (e.g., methane, ethane, propane, isobutene, pentane, n-hexane, biodiesel, bio-gasoline and mixtures thereof), co-products (e.g., proteins, such as cellulolytic proteins (enzymes) or single cell proteins), and mixtures of any of these in any combination or relative concentration, and optionally in combination with any additives (e.g., fuel additives). Other examples include carboxylic acids, salts of a carboxylic acid, a mixture of carboxylic acids and salts of carboxylic acids and esters of carboxylic acids (e.g., methyl, ethyl and n-propyl esters), ketones (e.g., acetone), aldehydes (e.g., acetaldehyde), alpha and beta unsaturated acids (e.g., acrylic acid) and olefins (e.g., ethylene). Other alcohols and alcohol derivatives include propanol, propylene glycol, 1,4-butanediol, 1,3-propanediol, sugar alcohols (e.g., erythritol, glycol, glycerol, sorbitol threitol, arabitol, ribitol, mannitol, dulcitol, fucitol, iditol, isomalt, maltitol, lactitol, xylitol and other polyols), and methyl or ethyl esters of any of these alcohols. Other products include methyl acrylate, methylmethacrylate, D-lactic acid, L-lactic acid, pyruvic acid, poly lactic acid, citric acid, formic acid, acetic acid, propionic acid, butyric acid, succinic acid, valeric acid, caproic acid, 3-hydroxypropionic acid, palmitic acid, stearic acid, oxalic acid, malonic acid, glutaric acid, oleic acid, linoleic acid, glycolic acid, gamma-hydroxybutyric acid, and mixtures thereof, salts of any of these acids, mixtures of any of the acids and their respective salts.

Any combination of the above products with each other, and/or of the above products with other products, which other products may be made by the processes described herein or otherwise, may be packaged together and sold as products. The products may be combined, e.g., mixed, blended or co-dissolved, or may simply be packaged or sold together.

Any of the products or combinations of products described herein may be sanitized or sterilized prior to selling the products, e.g., after purification or isolation or even after packaging, to neutralize one or more potentially undesirable contaminants that could be present in the product(s). Such sanitation can be done with electron bombardment, for example, be at a dosage of less than about 20 Mrad, e.g., from about 0.1 to 15 Mrad, from about 0.5 to 7 Mrad, or from about 1 to 3 Mrad.

The processes described herein can produce various byproduct streams useful for generating steam and electricity to be used in other parts of the plant (co-generation) or sold on the open market. For example, steam generated from burning by-product streams can be used in a distillation process. As another example, electricity generated from burning by-product streams can be used to power electron beam generators used in pretreatment.

The by-products used to generate steam and electricity are derived from a number of sources throughout the process. For example, anaerobic digestion of wastewater can produce a biogas high in methane and a small amount of waste biomass (sludge). As another example, post-saccharification and/or post-distillate solids (e.g., unconverted lignin, cellulose, and hemicellulose remaining from the pretreatment and primary processes) can be used, e.g., burned, as a fuel.

Other intermediates and products, including food and pharmaceutical products, are described in U.S. Pat. App. Pub. 2010/0124583 A1, published May 20, 2010, to Medoff, the full disclosure of which is hereby incorporated by reference herein.

Lignin Derived Products

The spent biomass (e.g., spent lignocellulosic material) from lignocellulosic processing by the methods described are expected to have a high lignin content and in addition to being useful for producing energy through combustion in a Co-Generation plant, may have uses as other valuable products. For example, the lignin can be used as captured as a plastic, or it can be synthetically upgraded to other plastics. In some instances, it can also be converted to lignosulfonates, which can be utilized as binders, dispersants, emulsifiers or sequestrants.

When used as a binder, the lignin or a lignosulfonate can, e.g., be utilized in coal briquettes, in ceramics, for binding carbon black, for binding fertilizers and herbicides, as a dust suppressant, in the making of plywood and particle board, for binding animal feeds, as a binder for fiberglass, as a binder in linoleum paste and as a soil stabilizer.

When used as a dispersant, the lignin or lignosulfonates can be used, for example in, concrete mixes, clay and ceramics, dyes and pigments, leather tanning and in gypsum board.

When used as an emulsifier, the lignin or lignosulfonates can be used, e.g., in asphalt, pigments and dyes, pesticides and wax emulsions.

As a sequestrant, the lignin or lignosulfonates can be used, e.g., in micro-nutrient systems, cleaning compounds and water treatment systems, e.g., for boiler and cooling systems.

For energy production lignin generally has a higher energy content than holocellulose (cellulose and hemicellulose) since it contains more carbon than homocellulose. For example, dry lignin can have an energy content of between about 11,000 and 12,500 BTU per pound, compared to 7,000 an 8,000 BTU per pound of holocellulose. As such, lignin can be densified and converted into briquettes and pellets for burning. For example, the lignin can be converted into pellets by any method described herein. For a slower burning pellet or briquette, the lignin can be crosslinked, such as applying a radiation dose of between about 0.5 Mrad and 5 Mrad. Crosslinking can make a slower burning form factor. The form factor, such as a pellet or briquette, can be converted to a "synthetic coal" or charcoal by pyrolyzing in the absence of air, e.g., at between 400 and 950° C. Prior to pyrolyzing, it can be desirable to crosslink the lignin to maintain structural integrity.

Saccharification

In order to convert the feedstock to a form that can be readily processed, the glucan- or xylan-containing cellulose in the feedstock can be hydrolyzed to low molecular weight carbohydrates, such as sugars, by a saccharifying agent, e.g., an enzyme or acid, a process referred to as saccharification. The low molecular weight carbohydrates can then be used, for example, in an existing manufacturing plant, such as a single cell protein plant, an enzyme manufacturing plant, or a fuel plant, e.g., an ethanol manufacturing facility.

The feedstock can be hydrolyzed using an enzyme, e.g., by combining the materials and the enzyme in a solvent, e.g., in an aqueous solution.

Alternatively, the enzymes can be supplied by organisms that break down biomass, such as the cellulose and/or the lignin portions of the biomass, contain or manufacture various cellulolytic enzymes (cellulases), ligninases or various small molecule biomass-degrading metabolites. These enzymes may be a complex of enzymes that act synergistically to degrade crystalline cellulose or the lignin portions of biomass. Examples of cellulolytic enzymes include: endoglucanases, cellobiohydrolases, and cellobiases (beta-glucosidases).

During saccharification a cellulosic substrate can be initially hydrolyzed by endoglucanases at random locations producing oligomeric intermediates. These intermediates are then substrates for exo-splitting glucanases such as cellobiohydrolase to produce cellobiose from the ends of the cellulose polymer. Cellobiose is a water-soluble 1,4-linked dimer of glucose. Finally, cellobiase cleaves cellobiose to yield glucose. The efficiency (e.g., time to hydrolyze and/or completeness of hydrolysis) of this process depends on the recalcitrance of the cellulosic material.

Therefore, the treated biomass materials can be saccharified, generally by combining the material and a cellulase enzyme in a fluid medium, e.g., an aqueous solution. In some cases, the material is boiled, steeped, or cooked in hot water prior to saccharification, as described in U.S. Pat. App. Pub. 2012/0100577 A1 by Medoff and Masterman, published on Apr. 26, 2012, the entire contents of which are incorporated herein.

The saccharification process can be partially or completely performed in a tank (e.g., a tank having a volume of at least 4000, 40,000, or 500,000 L) in a manufacturing plant, and/or can be partially or completely performed in transit, e.g., in a rail car, tanker truck, or in a supertanker or the hold of a ship. The time required for complete saccharification will depend on the process conditions and the carbohydrate-containing material and enzyme used. If saccharification is performed in a manufacturing plant under controlled conditions, the cellulose may be substantially entirely converted to sugar, e.g., glucose in about 12-96 hours. If saccharification is performed partially or completely in transit, saccharification may take longer.

It is generally preferred that the tank contents be mixed during saccharification, e.g., using jet mixing as described in International App. No. PCT/US2010/035331, filed May 18, 2010, which was published in English as WO 2010/135380 and designated the United States, the full disclosure of which is incorporated by reference herein.

The addition of surfactants can enhance the rate of saccharification. Examples of surfactants include non-ionic surfactants, such as a Tween® 20 or Tween® 80 polyethylene glycol surfactants, ionic surfactants, or amphoteric surfactants.

It is generally preferred that the concentration of the sugar solution resulting from saccharification be relatively high, e.g., greater than 40%, or greater than 50, 60, 70, 80, 90 or even greater than 95% by weight. Water may be removed, e.g., by evaporation, to increase the concentration of the sugar solution. This reduces the volume to be shipped, and also inhibits microbial growth in the solution.

Alternatively, sugar solutions of lower concentrations may be used, in which case it may be desirable to add an antimicrobial additive, e.g., a broad spectrum antibiotic, in a low concentration, e.g., 50 to 150 ppm. Other suitable antibiotics include amphotericin B, ampicillin, chloramphenicol, ciprofloxacin, gentamicin, hygromycin B, kanamycin, neomycin, penicillin, puromycin, streptomycin. Antibiotics will inhibit growth of microorganisms during transport and storage, and can be used at appropriate concentrations, e.g., between 15 and 1000 ppm by weight, e.g., between 25 and 500 ppm, or between 50 and 150 ppm. If desired, an antibiotic can be included even if the sugar concentration is relatively high. Alternatively, other additives with anti-microbial of preservative properties may be used. Preferably the antimicrobial additive(s) are food-grade.

A relatively high concentration solution can be obtained by limiting the amount of water added to the carbohydrate-containing material with the enzyme. The concentration can be controlled, e.g., by controlling how much saccharification takes place. For example, concentration can be increased by adding more carbohydrate-containing material to the solution. In order to keep the sugar that is being produced in solution, a surfactant can be added, e.g., one of those discussed above. Solubility can also be increased by increasing the temperature of the solution. For example, the solution can be maintained at a temperature of 40-50° C., 60-80° C., or even higher.

Saccharifying Agents

Suitable cellulolytic enzymes include cellulases from species in the genera *Bacillus, Coprinus, Myceliophthora, Cephalosporium, Scytalidium, Penicillium, Aspergillus, Pseudomonas, Humicola, Fusarium, Thielavia, Acremonium, Chrysosporium* and *Trichoderma*, especially those produced by a strain selected from the species *Aspergillus* (see, e.g., EP Pub. No. 0 458 162), *Humicola insolens* (reclassified as *Scytalidium thermophilum*, see, e.g., U.S. Pat. No. 4,435,307), *Coprinus cinereus, Fusarium oxysporum, Myceliophthora thermophila, Meripilus giganteus, Thielavia terrestris, Acremonium* sp. (including, but not limited to, *A. persicinum, A. acremonium, A. brachypenium, A. dichromosporum, A. obclavatum, A. pinkertoniae, A. roseogriseum, A. incoloratum,* and *A. furatum*). Preferred strains include *Humicola insolens* DSM 1800, *Fusarium oxysporum* DSM 2672, *Myceliophthora thermophila* CBS 117.65, *Cephalosporium* sp. RYM-202, *Acremonium* sp. CBS 478.94, *Acremonium* sp. CBS 265.95, *Acremonium persicinum* CBS 169.65, *Acremonium acremonium* AHU 9519, *Cephalosporium* sp. CBS 535.71, *Acremonium brachypenium* CBS 866.73, *Acremonium dichromosporum* CBS 683.73, *Acremonium obclavatum* CBS 311.74, *Acremonium pinkertoniae* CBS 157.70, *Acremonium roseogriseum* CBS 134.56, *Acremonium incoloratum* CBS 146.62, and *Acremonium furatum* CBS 299.70H. Cellulolytic enzymes may also be obtained from *Chrysosporium*, preferably a strain of *Chrysosporium lucknowense*. Additional strains that can be used include, but are not limited to, *Trichoderma* (particularly *T. viride, T. reesei,* and *T. koningii*), alkalophilic *Bacillus* (see, for example, U.S. Pat. No. 3,844,890 and EP Pub. No. 0 458 162), and *Streptomyces* (see, e.g., EP Pub. No. 0 458 162).

In addition to or in combination to enzymes, acids, bases and other chemicals (e.g., oxidants) can be utilized to saccharify lignocellulosic and cellulosic materials. These can be used in any combination or sequence (e.g., before, after and/or during addition of an enzyme). For example strong mineral acids can be utilized (e.g. HCl, $H_2SO_4$, $H_3PO_4$) and strong bases (e.g., NaOH, KOH).

Sugars

In the processes described herein, for example after saccharification, sugars (e.g., glucose and xylose) can be isolated. For example sugars can be isolated by precipitation, crystallization, chromatography (e.g., simulated moving bed chromatography, high pressure chromatography), centrifugation, extraction, any other isolation method known in the art, and combinations thereof.

Hydrogenation and Other Chemical Transformations

The processes described herein can include hydrogenation. For example glucose and xylose can be hydrogenated to sorbitol and xylitol respectively. Hydrogenation can be accomplished by use of a catalyst (e.g., Pt/gamma-$Al_2O_3$, Ru/C, Raney Nickel, or other catalysts know in the art) in combination with $H_2$ under high pressure (e.g., 10 to 12000 psi). Other types of chemical transformation of the products from the processes described herein can be used, for example production of organic sugar derived products (e.g., furfural and furfural-derived products). Chemical transformations of sugar derived products are described in U.S. Ser. No. 13/934,704 filed Jul. 3, 2013, the entire disclosure of which is incorporated herein by reference.

Fermentation

Yeast and *Zymomonas* bacteria, for example, can be used for fermentation or conversion of sugar(s) to alcohol(s). Other microorganisms are discussed below. The optimum pH for fermentations is about pH 4 to 7. For example, the optimum pH for yeast is from about pH 4 to 5, while the optimum pH for *Zymomonas* is from about pH 5 to 6. Typical fermentation times are about 24 to 168 hours (e.g., 24 to 96 hrs) with temperatures in the range of 20° C. to 40° C. (e.g., 26° C. to 40° C.), however thermophilic microorganisms prefer higher temperatures.

In some embodiments, e.g., when anaerobic organisms are used, at least a portion of the fermentation is conducted in the absence of oxygen, e.g., under a blanket of an inert gas such as $N_2$, Ar, He, $CO_2$ or mixtures thereof. Additionally, the mixture may have a constant purge of an inert gas flowing through the tank during part of or all of the fermentation. In some cases, anaerobic condition, can be achieved or maintained by carbon dioxide production during the fermentation and no additional inert gas is needed.

In some embodiments, all or a portion of the fermentation process can be interrupted before the low molecular weight sugar is completely converted to a product (e.g., ethanol). The intermediate fermentation products include sugar and carbohydrates in high concentrations. The sugars and carbohydrates can be isolated via any means known in the art. These intermediate fermentation products can be used in preparation of food for human or animal consumption. Additionally or alternatively, the intermediate fermentation products can be ground to a fine particle size in a stainless-steel laboratory mill to produce a flour-like substance. Jet mixing may be used during fermentation, and in some cases saccharification and fermentation are performed in the same tank.

Nutrients for the microorganisms may be added during saccharification and/or fermentation, for example the food-based nutrient packages described in U.S. Pat. App. Pub. 2012/0052536, filed Jul. 15, 2011, the complete disclosure of which is incorporated herein by reference.

"Fermentation" includes the methods and products that are disclosed in International application Nos. PCT/US2012/71093 published Jun. 27, 2013, PCT/US2012/71907 published Jun. 27, 2012, and PCT/US2012/71083 published Jun. 27, 2012 the contents of which are incorporated by reference herein in their entirety.

Mobile fermenters can be utilized, as described in International App. No. PCT/US2007/074028 (which was filed Jul. 20, 2007, was published in English as WO 2008/011598 and designated the United States) and has a U.S. issued U.S. Pat. No. 8,318,453, the contents of which are incorporated herein in its entirety. Similarly, the saccharification equipment can be mobile. Further, saccharification and/or fermentation may be performed in part or entirely during transit.

Fermentation Agents

The microorganism(s) used in fermentation can be naturally-occurring microorganisms and/or engineered microorganisms. For example, the microorganism can be a bacterium (including, but not limited to, e.g., a cellulolytic bacterium), a fungus, (including, but not limited to, e.g., a yeast), a plant, a protist, e.g., a protozoa or a fungus-like protest (including, but not limited to, e.g., a slime mold), or an alga. When the organisms are compatible, mixtures of organisms can be utilized.

Suitable fermenting microorganisms have the ability to convert carbohydrates, such as glucose, fructose, xylose, arabinose, mannose, galactose, oligosaccharides or polysaccharides into fermentation products. Fermenting microorganisms include strains of the genus *Saccharomyces* spp. (including, but not limited to, *S. cerevisiae* (baker's yeast), *S. distaticus, S. uvarum*), the genus *Kluyveromyces*, (including, but not limited to, *K. marxianus, K. fragilis*), the genus *Candida* (including, but not limited to, *C. pseudotropicalis*, and *C. brassicae*), *Pichia stipitis* (a relative of *Candida shehatae*), the genus *Clavispora* (including, but not limited to, *C. lusitaniae* and *C. opuntiae*), the genus *Pachysolen* (including, but not limited to, *P. tannophilus*), the genus *Bretannomyces* (including, but not limited to, e.g., *B. clausenii* (Philippidis, G. P., 1996, Cellulose bioconversion technology, in Handbook on Bioethanol: Production and Utilization, Wyman, C. E., ed., Taylor & Francis, Washington, D.C., 179-212)). Other suitable microorganisms include, for example, *Zymomonas mobilis, Clostridium* spp. (including, but not limited to, *C. thermocellum* (Philippidis, 1996, supra), *C. saccharobutylacetonicum, C. tyroburyricum C. saccharobutylicum, C. Puniceum, C. beijernckii*, and *C. acetoburylicum*), *Moniliella* spp. (including but not limited to *M. pollinis, M. tomentosa, M. madida, M. nigrescens, M. oedocephali, M. megachiliensis*), *Yarrowia lipolytica, Aureobasidium* sp., *Trichosporonoides* sp., *Trigonopsis variabilis, Trichosporon* sp., *Moniliellaacetoabutans* sp., *Typhula variabilis, Candida magnoliae, Ustilaginomycetes* sp., *Pseudozyma tsukubaensis*, yeast species of genera *Zygosaccharomyces, Debaryomyces, Hansenula* and *Pichia*, and fungi of the dematioid genus *Torula* (e.g., *T. corallina*).

Additional microorganisms include the *Lactobacillus* group. Examples include *Lactobacillus casei, Lactobacillus rhamnosus, Lactobacillus delbrueckii, Lactobacillus plantarum, Lactobacillus coryniformis*, e.g., *Lactobacillus coryniformis* subspecies *torquens, Lactobacillus pentosus, Lactobacillus brevis*. Other microorganisms include *Pediococus penosaceus, Rhizopus oryzae*.

Several organisms, such as bacteria, yeasts and fungi, can be utilized to ferment biomass derived products such as sugars and alcohols to succinic acid and similar products. For example, organisms can be selected from; *Actinobacillus succinogenes, Anaerobiospirillum succiniciproducens, Mannheimia succiniciproducens, Ruminococcus flaverfaciens, Ruminococcus albus, Fibrobacter succiunogenes,*

*Bacteroides fragilis, Bacteroides ruminicola, Bacteroides amylophilus, Bacteroides succinogenes, Mannheimia succiniciproducens, Corynebacterium glutamicum, Aspergillus niger, Aspergillus fumigatus, Byssochlamys nivea, Lentinus degener, Paecilomyces varioti, Penicillium viniferum, Saccharomyces cerevisiae, Enterococcus faecali, Prevotella ruminicolas, Debaryomyces hansenii, Candida catenulata* VKM Y-5, *C. mycoderma* VKM Y-240, *C. rugosa* VKM Y-67, *C. paludigena* VKM Y-2443, *C. utilis* VKM Y-74, *C. utilis* 766, *C. zeylanoides* VKM Y-6, *C. zeylanoides* VKM Y-14, *C. zeylanoides* VKM Y-2324, *C. zeylanoides* VKM Y-1543, *C. zeylanoides* VKM Y-2595, *C. valida* VKM Y-934, *Kluyveromyces wickerhamii* VKM Y-589, *Pichia anomala* VKM Y-118, *P. besseyi* VKM Y-2084, *P. media* VKM Y-1381, *P. guilliermondii* H-P-4, *P. guilliermondii* 916, *P. inositovora* VKM Y-2494, *Saccharomyces cerevisiae* VKM Y-381, *Torulopsis candida* 127, *T. candida* 420, *Yarrowia lipolytica* 12a, *Y. lipolytica* VKM Y-47, *Y. lipolytica* 69, *Y. lipolytica* VKM Y-57, *Y. lipolytica* 212, *Y. lipolytica* 374/4, *Y. lipolytica* 585, *Y. lipolytica* 695, *Y. lipolytica* 704, and mixtures of these organisms.

Many such microbial strains are publicly available, either commercially or through depositories such as the ATCC (American Type Culture Collection, Manassas, Va., USA), the NRRL (Agricultural Research Service Culture Collection, Peoria, Ill., USA), or the DSMZ (Deutsche Sammlung von Mikroorganismen und Zellkulturen GmbH, Braunschweig, Germany), to name a few.

Commercially available yeasts include, for example, RED STAR®/Lesaffre Ethanol Red (available from Red Star/Lesaffre, USA), FALI® (available from Fleischmann's Yeast, a division of Burns Philip Food Inc., USA), SUPERSTART® (available from Alltech, now Lalemand), GERT STRAND® (available from Gert Strand AB, Sweden) and FERMOL® (available from DSM Specialties).

Distillation

After fermentation, the resulting fluids can be distilled using, for example, a "beer column" to separate ethanol and other alcohols from the majority of water and residual solids. The vapor exiting the beer column can be, e.g., 35% by weight ethanol and can be fed to a rectification column. A mixture of nearly azeotropic (92.5%) ethanol and water from the rectification column can be purified to pure (99.5%) ethanol using vapor-phase molecular sieves. The beer column bottoms can be sent to the first effect of a three-effect evaporator. The rectification column reflux condenser can provide heat for this first effect. After the first effect, solids can be separated using a centrifuge and dried in a rotary dryer. A portion (25%) of the centrifuge effluent can be recycled to fermentation and the rest sent to the second and third evaporator effects. Most of the evaporator condensate can be returned to the process as fairly clean condensate with a small portion split off to waste water treatment to prevent build-up of low-boiling compounds.

Hydrocarbon-Containing Materials

In other embodiments utilizing the methods and systems described herein, hydrocarbon-containing materials can be processed. Any process described herein can be used to treat any hydrocarbon-containing material herein described. "Hydrocarbon-containing materials," as used herein, is meant to include oil sands, oil shale, tar sands, coal dust, coal slurry, bitumen, various types of coal, and other naturally-occurring and synthetic materials that include both hydrocarbon components and solid matter. The solid matter can include wood, rock, sand, clay, stone, silt, drilling slurry, or other solid organic and/or inorganic matter. The term can also include waste products such as drilling waste and by-products, refining waste and by-products, or other waste products containing hydrocarbon components, such as asphalt shingling and covering, asphalt pavement, etc.

In yet other embodiments utilizing the methods and systems described herein, wood and wood containing produces can be processed. For example lumber products can be processed, e.g. boards, sheets, laminates, beams, particle boards, composites, rough cut wood, soft wood and hard wood. In addition cut trees, bushes, wood chips, saw dust, roots, bark, stumps, decomposed wood and other wood containing biomass material can be processed.

Conveying Systems

Various conveying systems can be used to convey the biomass material, for example, as discussed, to a vault, and under an electron beam in a vault. Exemplary conveyors are belt conveyors, pneumatic conveyors, screw conveyors, carts, trains, trains or carts on rails, elevators, front loaders, backhoes, cranes, various scrapers and shovels, trucks, and throwing devices can be used. For example, vibratory conveyors can be used in various processes described herein. Vibratory conveyors are described in PCT/US2013/64289 filed Oct. 10, 2013 the full disclosure of which is incorporated by reference herein.

Vibratory conveyors are particularly useful for spreading the material and producing a uniform layer on the conveyor trough surface. For example the initial feedstock can form a pile of material that can be at least four feet high (e.g., at least about 3 feet, at least about 2 feet, at least about 1 foot, at least about 6 inches, at least about 5 inches, at least about, 4 inches, at least about 3 inches, at least about 2 inches, at least about 1 inch, at least about t inch) and spans less than the width of the conveyor (e.g., less than about 10%, less than about 20%, less than about 30%, less than about 40%, less than about 50%, less than about 60%, less than about 70%, less than about 80%, less than about 90%, less than about 95%, less than about 99%). The vibratory conveyor can spread the material to span the entire width of the conveyor trough and have a uniform thickness, preferably as discussed above. In some cases, an additional spreading method can be useful. For example, a spreader such as a broadcast spreader, a drop spreader (e.g., a CHRISTY SPREADER™) or combinations thereof can be used to drop (e.g., place, pour, spill and/or sprinkle) the feedstock over a wide area. Optionally, the spreader can deliver the biomass as a wide shower or curtain onto the vibratory conveyor. Additionally, a second conveyor, upstream from the first conveyor (e.g., the first conveyor is used in the irradiation of the feedstock), can drop biomass onto the first conveyor, where the second conveyor can have a width transverse to the direction of conveying smaller than the first conveyor. In particular, when the second conveyor is a vibratory conveyor, the feedstock is spread by the action of the second and first conveyor. In some optional embodiments, the second conveyor ends in a bias cross cut discharge (e.g., a bias cut with a ratio of 4:1) so that the material can be dropped as a wide curtain (e.g., wider than the width of the second conveyor) onto the first conveyor. The initial drop area of the biomass by the spreader (e.g., broadcast spreader, drop spreader, conveyor, or cross cut vibratory conveyor) can span the entire width of the first vibratory conveyor, or it can span part of this width. Once dropped onto the conveyor, the material is spread even more uniformly by the vibrations of the conveyor so that, preferably, the entire width of the conveyor is covered with a uniform layer of biomass. In some embodiments combinations of spreaders can be used. Some methods of spreading a feed stock are described in U.S. Pat. No. 7,153,533, filed Jul. 23, 2002 and published Dec. 26, 2006, the entire disclosure of which is incorporated herein by reference.

Generally, it is preferred to convey the material as quickly as possible through an electron beam to maximize throughput. For example, the material can be conveyed at rates of at least 1 ft/min, e.g., at least 2 ft/min, at least 3 ft/min, at least 4 ft/min, at least 5 ft/min, at least 10 ft/min, at least 15 ft/min, at least 20 ft/min, at least 25 ft/min, at least 30 ft/min, at least 40 ft/min, at least 50 ft/min, at least 60 ft/min, at least 70 ft/min, at least 80 ft/min, at least 90 ft/min. The rate of conveying is related to the beam current and targeted irradiation dose, for example, for a ¼ inch thick biomass spread over a 5.5 foot wide conveyor and 100 mA, the conveyor can move at about 20 ft/min to provide a useful irradiation dosage (e.g. about 10 Mrad for a single pass), at 50 mA the conveyor can move at about 10 ft/min to provide approximately the same irradiation dosage.

The rate at which material can be conveyed depends on the shape and mass of the material being conveyed, and the desired treatment. Flowing materials e.g., particulate materials, are particularly amenable to conveying with vibratory conveyors. Conveying speeds can, for example be, at least 100 lb/hr (e.g., at least 500 lb/hr, at least 1000 lb/hr, at least 2000 lb/hr, at least 3000 lb/hr, at least 4000 lb/hr, at least 5000 lb/hr, at least 10,000 lb/hr, at least 15,000 lb/hr, or even at least 25,000 lb/hr). Some typical conveying speeds can be between about 1000 and 10,000 lb/hr, (e.g., between about 1000 lb/hr and 8000 lb/hr, between about 2000 and 7000 lb/hr, between about 2000 and 6000 lb/hr, between about 2000 and 5000 lb/hr, between about 2000 and 4500 lb/hr, between about 1500 and 5000 lb/hr, between about 3000 and 7000 lb/hr, between about 3000 and 6000 lb/hr, between about 4000 and 6000 lb/hr and between about 4000 and 5000 lb/hr). Typical conveying speeds depend on the density of the material. For example, for a biomass with a density of about 35 lb/ft3, and a conveying speed of about 5000 lb/hr, the material is conveyed at a rate of about 143 ft3/hr, if the material is ¼" thick and is in a trough 5.5 ft wide, the material is conveyed at a rate of about 1250 ft/hr (about 21 ft/min). Rates of conveying the material can therefore vary greatly. Preferably, for example, a ¼" thick layer of biomass, is conveyed at speeds of between about 5 and 100 ft/min (e.g. between about 5 and 100 ft/min, between about 6 and 100 ft/min, between about 7 and 100 ft/min, between about 8 and 100 ft/min, between about 9 and 100 ft/min, between about 10 and 100 ft/min, between about 11 and 100 ft/min, between about 12 and 100 ft/min, between about 13 and 100 ft/min, between about 14 and 100 ft/min, between about 15 and 100 ft/min, between about 20 and 100 ft/min, between about 30 and 100 ft/min, between about 40 and 100 ft/min, between about 2 and 60 ft/min, between about 3 and 60 ft/min, between about 5 and 60 ft/min, between about 6 and 60 ft/min, between about 7 and 60 ft/min, between about 8 and 60 ft/min, between about 9 and 60 ft/min, between about 10 and 60 ft/min, between about 15 and 60 ft/min, between about 20 and 60 ft/min, between about 30 and 60 ft/min, between about 40 and 60 ft/min, between about 2 and 50 ft/min, between about 3 and 50 ft/min, between about 5 and 50 ft/min, between about 6 and 50 ft/min, between about 7 and 50 ft/min, between about 8 and 50 ft/min, between about 9 and 50 ft/min, between about 10 and 50 ft/min, between about 15 and 50 ft/min, between about 20 and 50 ft/min, between about 30 and 50 ft/min, between about 40 and 50 ft/min). It is preferable that the material be conveyed at a constant rate, for example, to help maintain a constant irradiation of the material as it passes under the electron beam (e.g., shower, field).

The vibratory conveyors described can include screens used for sieving and sorting materials. Port openings on the side or bottom of the troughs can be used for sorting, selecting or removing specific materials, for example, by size or shape. Some conveyors have counterbalances to reduce the dynamic forces on the support structure. Some vibratory conveyors are configured as spiral elevators, are designed to curve around surfaces and/or are designed to drop material from one conveyor to another (e.g., in a step, cascade or as a series of steps or a stair). Along with conveying materials conveyors can be used, by themselves or coupled with other equipment or systems, for screening, separating, sorting, classifying, distributing, sizing, inspection, picking, metal removing, freezing, blending, mixing, orienting, heating, cooking, drying, dewatering, cleaning, washing, leaching, quenching, coating, de-dusting and/or feeding. The conveyors can also include covers (e.g., dust-tight covers), side discharge gates, bottom discharge gates, special liners (e.g., anti-stick, stainless steel, rubber, custom steal, and or grooved), divided troughs, quench pools, screens, perforated plates, detectors (e.g., metal detectors), high temperature designs, food grade designs, heaters, dryers and or coolers. In addition, the trough can be of various shapes, for example, flat bottomed, vee shaped bottom, flanged at the top, curved bottom, flat with ridges in any direction, tubular, half pipe, covered or any combinations of these. In particular, the conveyors can be coupled with an irradiation systems and/or equipment.

The conveyors (e.g., vibratory conveyor) can be made of corrosion resistant materials. The conveyors can utilize structural materials that include stainless steel (e.g., 304, 316 stainless steel, HASTELLOY® ALLOYS and INCONEL® Alloys). For example, HASTELLOY® Corrosion-Resistant alloys from Hynes (Kokomo, Ind., USA) such as HASTELLOY® B-3® ALLOY, HASTELLOY® HYBRID-BC 1® ALLOY, HASTELLOY® C-4 ALLOY, HASTELLOY® C-22® ALLOY, HASTELLOY® C-22HS® ALLOY, HASTELLOY® C-276 ALLOY, HASTELLOY® C-2000® ALLOY, HASTELLOY® G-30® ALLOY, HASTELLOY® G-35® ALLOY, HASTELLOY® N ALLOY and HASTELLOY® ULTIMET® alloy.

The vibratory conveyors can include non-stick release coatings, for example, TUFFLON™ (Dupont, Del., USA). The vibratory conveyors can also include corrosion resistant coatings. For example, coatings that can be supplied from Metal Coatings Corp (Houston, Tex., USA) and others such as Fluoropolymer, XYLAN®, Molybdenum Disulfide, Epoxy Phenolic, Phosphate-ferrous metal coating, Polyurethane-high gloss topcoat for epoxy, inorganic zinc, Poly Tetrafluoro ethylene, PPS/RYTON®, fluorinated ethylene propylene, PVDF/DYKOR®, ECTFE/HALAR® and Ceramic Epoxy Coating. The coatings can improve resistance to process gases (e.g., ozone), chemical corrosion, pitting corrosion, galling corrosion and oxidation.

Optionally, in addition to the conveying systems described herein, one or more other conveying systems can be enclosed. When using an enclosure, the enclosed conveyor can also be purged with an inert gas so as to maintain an atmosphere at a reduced oxygen level. Keeping oxygen levels low avoids the formation of ozone which in some instances is undesirable due to its reactive and toxic nature.

For example, the oxygen can be less than about 20% (e.g., less than about 10%, less than about 1%, less than about 0.1%, less than about 0.01%, or even less than about 0.001% oxygen). Purging can be done with an inert gas including, but not limited to, nitrogen, argon, helium or carbon dioxide. This can be supplied, for example, from a boil off of a liquid source (e.g., liquid nitrogen or helium), generated or separated from air in situ, or supplied from tanks. The inert gas can be recirculated and any residual oxygen can be removed using a catalyst, such as a copper catalyst bed. Alternatively, combinations of purging, recirculating and oxygen removal can be done to keep the oxygen levels low.

The enclosed conveyor can also be purged with a reactive gas that can react with the biomass. This can be done before, during or after the irradiation process. The reactive gas can be, but is not limited to, nitrous oxide, ammonia, oxygen, ozone, hydrocarbons, aromatic compounds, amides, peroxides, azides, halides, oxyhalides, phosphides, phosphines, arsines, sulfides, thiols, boranes and/or hydrides. The reactive gas can be activated in the enclosure, e.g., by irradiation (e.g., electron beam, UV irradiation, microwave irradiation, heating, IR radiation), so that it reacts with the biomass. The biomass itself can be activated, for example by irradiation. Preferably the biomass is activated by the electron beam, to produce radicals which then react with the activated or unactivated reactive gas, e.g., by radical coupling or quenching.

Purging gases supplied to an enclosed conveyor can also be cooled, for example below about 25° C., below about 0° C., below about −40° C., below about −80° C., below about −120° C. For example, the gas can be boiled off from a compressed gas such as liquid nitrogen or sublimed from solid carbon dioxide. As an alternative example, the gas can be cooled by a chiller or part of or the entire conveyor can be cooled.

OTHER EMBODIMENTS

Any material, processes or processed materials discussed herein can be used to make products and/or intermediates such as composites, fillers, binders, plastic additives, adsorbents and controlled release agents. The methods can include densification, for example, by applying pressure and heat to the materials. For example composites can be made by combining fibrous materials with a resin or polymer. For example radiation cross-linkable resin, e.g., a thermoplastic resin can be combined with a fibrous material to provide a fibrous material/cross-linkable resin combination. Such materials can be, for example, useful as building materials, protective sheets, containers and other structural materials (e.g., molded and/or extruded products). Absorbents can be, for example, in the form of pellets, chips, fibers and/or sheets. Adsorbents can be used, for example, as pet bedding, packaging material or in pollution control systems. Controlled release matrices can also be the form of, for example, pellets, chips, fibers and or sheets. The controlled release matrices can, for example, be used to release drugs, biocides, fragrances. For example, composites, absorbents and control release agents and their uses are described in International Serial No. PCT/US2006/010648, filed Mar. 23, 2006, and U.S. Pat. No. 8,074,910 filed Nov. 22, 2011, the entire disclosures of which are herein incorporated by reference.

In some instances the biomass material is treated at a first level to reduce recalcitrance, e.g., utilizing accelerated electrons, to selectively release one or more sugars (e.g., xylose). The biomass can then be treated to a second level to release one or more other sugars (e.g., glucose). Optionally the biomass can be dried between treatments. The treatments can include applying chemical and biochemical treatments to release the sugars. For example, a biomass material can be treated to a level of less than about 20 Mrad (e.g., less than about 15 Mrad, less than about 10 Mrad, less than about 5 Mrad, less than about 2 Mrad) and then treated with a solution of sulfuric acid, containing less than 10% sulfuric acid (e.g., less than about 9%., less than about 8%, less than about 7%, less than about 6%, less than about 5%, less than about 4%, less than about 3%, less than about 2%, less than about 1%, less than about 0.75%, less than about 0.50%, less than about 0.25%) to release xylose. Xylose, for example that is released into solution, can be separated from solids and optionally the solids washed with a solvent/solution (e.g., with water and/or acidified water). Optionally, the Solids can be dried, for example in air and/or under vacuum optionally with heating (e.g., below about 150 deg C., below about 120 deg C.) to a water content below about 25 wt. % (below about 20 wt. %, below about 15 wt. %, below about 10 wt. %, below about 5 wt. %). The solids can then be treated with a level of less than about 30 Mrad (e.g., less than about 25 Mrad, less than about 20 Mrad, less than about 15 Mrad, less than about 10 Mrad, less than about 5 Mrad, less than about 1 Mrad or even not at all) and then treated with an enzyme (e.g., a cellulase) to release glucose. The glucose (e.g., glucose in solution) can be separated from the remaining solids. The solids can then be further processed, for example utilized to make energy or other products (e.g., lignin derived products).

Flavors, Fragrances and Colorants

Any of the products and/or intermediates described herein, for example, produced by the processes, systems and/or equipment described herein, can be combined with flavors, fragrances, colorants and/or mixtures of these. For example, any one or more of (optionally along with flavors, fragrances and/or colorants) sugars, organic acids, fuels, polyols, such as sugar alcohols, biomass, fibers and composites can be combined with (e.g., formulated, mixed or reacted) or used to make other products. For example, one or more such product can be used to make soaps, detergents, candies, drinks (e.g., cola, wine, beer, liquors such as gin or vodka, sports drinks, coffees, teas), syrups, pharmaceuticals, adhesives, sheets (e.g., woven, none woven, filters, tissues) and/or composites (e.g., boards). For example, one or more such product can be combined with herbs, flowers, petals, spices, vitamins, potpourri, or candles. For example, the formulated, mixed or reacted combinations can have flavors/fragrances of grapefruit, orange, apple, raspberry, banana, lettuce, celery, cinnamon, chocolate, vanilla, peppermint, mint, onion, garlic, pepper, saffron, ginger, milk, wine, beer, tea, lean beef, fish, clams, olive oil, coconut fat, pork fat, butter fat, beef bouillon, legume, potatoes, marmalade, ham, coffee and cheeses.

Flavors, fragrances and colorants can be added in any amount, such as between about 0.001 wt. % to about 30 wt. %, e.g., between about 0.01 to about 20, between about 0.05 to about 10, or between about 0.1 wt. % to about 5 wt. %. These can be formulated, mixed and or reacted (e.g., with any one of more product or intermediate described herein) by any means and in any order or sequence (e.g., agitated, mixed, emulsified, gelled, infused, heated, sonicated, and/or suspended). Fillers, binders, emulsifier, antioxidants can also be utilized, for example protein gels, starches and silica.

In one embodiment the flavors, fragrances and colorants can be added to the biomass immediately after the biomass is irradiated such that the reactive sites created by the irradiation may react with reactive compatible sites of the flavors, fragrances, and colorants.

The flavors, fragrances and colorants can be natural and/or synthetic materials. These materials can be one or more of a compound, a composition or mixtures of these (e.g., a formulated or natural composition of several compounds). Optionally the flavors, fragrances, antioxidants and colorants can be derived biologically, for example, from a fermentation process (e.g., fermentation of saccharified materials as described herein). Alternatively, or additionally these flavors, fragrances and colorants can be harvested from a whole organism (e.g., plant, fungus, animal, bacteria or yeast) or a part of an organism. The organism can be collected and or extracted to provide color, flavors, fragrances and/or antioxidant by any means including utilizing the methods, systems and equipment described herein, hot water extraction, supercritical fluid extraction, chemical extraction (e.g., solvent or reactive extraction including acids and bases), mechanical extraction (e.g., pressing, comminuting, filtering), utilizing an enzyme, utilizing a bacteria such as to break down a starting material, and combinations of these methods. The compounds can be derived by a chemical reaction, for example, the combination of a sugar (e.g., as produced as described herein) with an amino acid (Maillard reaction). The flavor, fragrance, antioxidant and/or colorant can be an intermediate and or product produced by the methods, equipment or systems described herein, for example and ester and a lignin derived product.

Some examples of flavor, fragrances or colorants are polyphenols. Polyphenols are pigments responsible for the red, purple and blue colorants of many fruits, vegetables, cereal grains, and flowers. Polyphenols also can have antioxidant properties and often have a bitter taste. The antioxidant properties make these important preservatives. On class of polyphenols are the flavonoids, such as Anthocyanidines, flavanonols, flavan-3-ols, s, flavanones and flavanonols. Other phenolic compounds that can be used include phenolic acids and their esters, such as chlorogenic acid and polymeric tannins.

Among the colorants inorganic compounds, minerals or organic compounds can be used, for example titanium dioxide, zinc oxide, aluminum oxide, cadmium yellow (E.g., CdS), cadmium orange (e.g., CdS with some Se), alizarin crimson (e.g., synthetic or non-synthetic rose madder), ultramarine (e.g., synthetic ultramarine, natural ultramarine, synthetic ultramarine violet), cobalt blue, cobalt yellow, cobalt green, viridian (e.g., hydrated chromium(III)oxide), chalcophylite, conichalcite, comubite, cornwallite and liroconite. Black pigments such as carbon black and self-dispersed blacks may be used.

Some flavors and fragrances that can be utilized include ACALEA TBHQ, ACET C-6, ALLYL AMYL GLYCOLATE, ALPHA TERPINEOL, AMBRETTOLIDE, AMBRINOL 95, ANDRANE, APHERMATE, APPLELIDE, BACDANOL®, BERGAMAL, BETA IONONE EPOXIDE, BETA NAPHTHYL ISO-BUTYL ETHER, BICYCLONONALACTONE, BORNAFIX®, CANTHOXAL, CASHMERAN®, CASHMERAN® VELVET, CASSIFFIX®, CEDRAFIX, CEDRAMBER®, CEDRYL ACETATE, CELESTOLIDE, CINNAMALVA, CITRAL DIMETHYL ACETATE, CITROLATE™, CITRONELLOL 700, CITRONELLOL 950, CITRONELLOL COEUR, CITRONELLYL ACETATE, CITRONELLYL ACETATE PURE, CITRONELLYL FORMATE, CLARYCET, CLONAL, CONIFERAN, CONIFERAN PURE, CORTEX ALDEHYDE 50% PEOMOSA, CYCLABUTE, CYCLACET®, CYCLAPROP®, CYCLEMAX™, CYCLOHEXYL ETHYL ACETATE, DAMASCOL, DELTA DAMASCONE, DIHYDRO CYCLACET, DIHYDRO MYRCENOL, DIHYDRO TERPINEOL, DIHYDRO TERPINYL ACETATE, DIMETHYL CYCLORMOL, DIMETHYL OCTANOL PQ, DIMYRCETOL, DIOLA, DIPENTENE, DULCINYL® RECRYSTALLIZED, ETHYL-3-PHENYL GLYCIDATE, FLEURAMONE, FLEURANIL, FLORAL SUPER, FLORALOZONE, FLORIFFOL, FRAISTONE, FRUCTONE, GALAXOLIDE® 50, GALAXOLIDE® 50 BB, GALAXOLIDE® 50 IPM, GALAXOLIDE® UNDILUTED, GALBASCONE, GERALDEHYDE, GERANIOL 5020, GERANIOL 600 TYPE, GERANIOL 950, GERANIOL 980 (PURE), GERANIOL CFT COEUR, GERANIOL COEUR, GERANYL ACETATE COEUR, GERANYL ACETATE, PURE, GERANYL FORMATE, GRISALVA, GUAIYL ACETATE, HELIONAL™, HERBAC, HERBALIME™, HEXADECANOLIDE, HEXALON, HEXENYL SALICYLATE CIS 3-, HYACINTH BODY, HYACINTH BODY NO. 3, HYDRATROPIC ALDEHYDE.DMA, HYDROXYOL, INDOLAROME, INTRELEVEN ALDEHYDE, INTRELEVEN ALDEHYDE SPECIAL, IONONE ALPHA, IONONE BETA, ISO CYCLO CITRAL, ISO CYCLO GERANIOL, ISO E SUPER®, ISOBUTYL QUINOLINE. JASMAL, JESSEMAL®, KHARISMAL®, KHARISMAL® SUPER, KHUSINIL, KOAVONE®, KOHINOOL®, LIFFAROME™, LIMOXAL, LINDENOL™, LYRAL®, LYRAME SUPER, MANDARIN ALD 10% TRI ETH, CITR, MARITIMA, MCK CHINESE, MEIJIFF™, MELAFLEUR, MELOZONE, METHYL ANTHRANILATE, METHYL IONONE ALPHA EXTRA, METHYL IONONE GAMMA A, METHYL IONONE GAMMA COEUR, METHYL IONONE GAMMA PURE, METHYL LAVENDER KETONE, MONTAVERDI®, MUGUESIA, MUGUET ALDEHYDE 50, MUSK Z4, MYRAC ALDEHYDE, MYRCENYL ACETATE, NECTARATE™, NEROL 900, NERYL ACETATE, OCIMENE, OCTACETAL, ORANGE FLOWER ETHER, ORIVONE, ORRINIFF 25%, OXASPIRANE, OZOFLEUR, PAMPLEFLEUR®, PEOMOSA, PHENOXANOL®, PICONIA, PRECYCLEMONE B, PRENYL ACETATE, PRISMANTOL, RESEDA BODY, ROSALVA, ROSAMUSK, SANJINOL, SANTALIFF™, SYVERTAL, TERPINEOL, TERPINOLENE 20, TERPINOLENE 90 PQ, TERPINOLENE RECT., TERPINYL ACETATE, TERPINYL ACETATE JAX, TETRAHYDRO, MUGUOL®, TETRAHYDRO MYRCENOL, TETRAMERAN, TIMBERSILK™, TOBACAROL, TRIMOFIX® O TT, TRIPLAL®, TRISAMBER®, VANORIS, VERDOX™, VERDOX™ HC, VERTENEX®, VERTENEX® HC, VERTOFIX® COEUR, VERTOLIFF, VERTOLIFF ISO, VIOLIFF, VIVALDIE, ZENOLIDE, ABS INDIA 75 PCT MIGLYOL, ABS MOROCCO 50 PCT DPG, ABS MOROCCO 50 PCT TEC, ABSOLUTE FRENCH, ABSOLUTE INDIA, ABSOLUTE MD 50 PCT BB, ABSOLUTE MOROCCO, CONCENTRATE PG, TINCTURE 20 PCT, AMBERGRIS, AMBRETTE ABSOLUTE, AMBRETTE SEED OIL, ARMOISE OIL 70 PCT THUYONE, BASIL ABSOLUTE GRAND VERT, BASIL GRAND VERT ABS MD, BASIL OIL GRAND VERT, BASIL OIL VERVEINA, BASIL OIL VIETNAM, BAY OIL TERPENELESS, BEESWAX ABS N G, BEESWAX ABSOLUTE, BENZOIN RESINOID SIAM, BENZOIN RESINOID SIAM 50 PCT DPG, BENZOIN RESINOID SIAM 50 PCT PG, BENZOIN RESINOID SIAM 70.5 PCT TEC, BLACKCURRANT BUD ABS 65 PCT PG, BLACKCURRANT BUD ABS MD 37 PCT TEC, BLACKCURRANT BUD ABS MIGLYOL, BLACKCURRANT BUD ABSOLUTE BURGUNDY, BOIS DE ROSE OIL, BRAN ABSOLUTE, BRAN RESINOID, BROOM ABSOLUTE ITALY, CARDAMOM GUATEMALA CO2 EXTRACT, CARDAMOM OIL GUATEMALA, CARDAMOM OIL INDIA, CARROT HEART, CASSIE ABSOLUTE EGYPT, CASSIE ABSOLUTE MD 50 PCT IPM, CASTOREUM ABS 90 PCT TEC, CASTOREUM ABS C 50 PCT MIOGLYOL, CASTOREUM ABSOLUTE, CASTOREUM RESINOID, CASTOREUM RESINOID 50 PCT DPG, CEDROL CEDRENE, CEDRUS ATLANTICA OIL REDIST, CHAMOMILE OIL ROMAN, CHAMOMILE OIL WILD, CHAMOMILE OIL WILD LOW LIMONENE, CINNAMON BARK OIL CEYLAN, CISTE ABSOLUTE, CISTE ABSOLUTE COLORLESS, CITRONELLA OIL ASIA IRON FREE, CIVET ABS 75 PCT PG, CIVET ABSOLUTE, CIVET TINCTURE 10 PCT, CLARY SAGE ABS FRENCH DECOL, CLARY SAGE ABSOLUTE FRENCH, CLARY SAGE CLESS 50 PCT PG, CIARY SAGE OIL FRENCH, COPAIBA BALSAM, COPAIBA BALSAM OIL, CORIANDER SEED OIL, CYPRESS OIL, CYPRESS OIL ORGANIC, DAVANA OIL, GALBANOL, GALBANUM ABSOLUTE COLORLESS, GALBANUM OIL, GALBANUM RESINOID, GALBANUM RESINOID 50 PCT DPG, GALBANUM RESINOID HERCOLYN BHT, GALBANUM RESINOID TEC BHT, GENTIANE ABSOLUTE MD 20 PCT BB, GENTIANE CONCRETE, GERANIUM ABS EGYPT MD, GERANIUM ABSOLUTE EGYPT, GERANIUM OIL CHINA, GERANIUM OIL EGYPT, GINGER OIL 624, GINGER OIL RECTIFIED SOLUBLE, GUAIACWOOD HEART, HAY ABS MD 50 PCT BB, HAY ABSOLUTE, HAY ABSOLUTE MD 50 PCT TEC, HEALINGWOOD, HYSSOP OIL ORGANIC, IMMORTELLE ABS YUGO MD 50 PCT TEC, IMMORTELLE ABSOLUTE SPAIN, IMMORTELLE ABSOLUTE YUGO, JASMIN ABS INDIA MD, JASMIN ABSOLUTE EGYPT, JASMIN ABSOLUTE INDIA, ASMIN ABSOLUTE MOROCCO, JASMIN ABSOLUTE SAMBAC, JONQUILLE ABS MD 20 PCT BB, JONQUILLE ABSOLUTE France, JUNIPER BERRY OIL FLG, JUNIPER BERRY OIL RECTIFIED SOLUBLE, LABDANUM RESINOID 50 PCT TEC, LABDANUM RESINOID BB, LABDANUM RESINOID MD, LABDANUM RESINOID MD 50 PCT BB, LAVANDIN ABSOLUTE H, LAVANDIN ABSOLUTE MD, LAVANDIN OIL ABRIAL ORGANIC, LAVANDIN OIL GROSSO ORGANIC, LAVANDIN OIL SUPER, LAVENDER ABSOLUTE H, LAVENDER ABSOLUTE MD, LAVENDER OIL COUMARIN FREE, LAVENDER OIL COUMARIN FREE ORGANIC, LAVENDER OIL MAILLETTE ORGANIC, LAVENDER OIL MT, MACE ABSOLUTE BB, MAGNOLIA FLOWER OIL LOW METHYL EUGENOL, MAGNOLIA FLOWER OIL, MAGNOLIA FLOWER OIL MD, MAGNOLIA LEAF OIL, MANDARIN OIL MD, MANDARIN OIL MD BHT, MATE ABSOLUTE BB, MOSS TREE ABSOLUTE MD TEX IFRA 43, MOSS-OAK ABS MD TEC IFRA 43, MOSS-OAK ABSOLUTE IFRA 43, MOSS-TREE ABSOLUTE MD IPM IFRA 43, MYRRH RESINOID BB, MYRRH RESINOID MD, MYRRH RESINOID TEC, MYRTLE OIL IRON FREE, MYRTLE OIL TUNISIA RECTIFIED, NARCISSE ABS MD 20 PCT BB, NARCISSE ABSOLUTE FRENCH, NEROLI OIL TUNISIA, NUTMEG OIL TERPENELESS, OEILLET ABSOLUTE, OLIBANUM RESINOID, OLIBANUM RESINOID BB, OLIBANUM RESINOID DPG, OLIBANUM RESINOID EXTRA 50 PCT DPG, OLIBANUM RESINOID MD, OLIBANUM RESINOID MD 50 PCT DPG, OLIBANUM RESINOID TEC, OPOPONAX RESINOID TEC, ORANGE BIGARADE OIL MD BHT, ORANGE BIGARADE OIL MD SCFC, ORANGE FLOWER ABSOLUTE TUNISIA, ORANGE FLOWER WATER ABSOLUTE TUNISIA, ORANGE LEAF ABSOLUTE, ORANGE LEAF WATER ABSOLUTE TUNISIA, ORRIS ABSOLUTE ITALY, ORRIS CONCRETE 15 PCT IRONE, ORRIS CONCRETE 8 PCT IRONE, ORRIS NATURAL 15 PCT IRONE 4095C, ORRIS NATURAL 8 PCT IRONE 2942C, ORRIS RESINOID, OSMANTHUS ABSOLUTE, OSMANTHUS ABSOLUTE MD 50 PCT BB, PATCHOULI HEART N° 3, PATCHOULI OIL INDONESIA, PATCHOULI OIL INDONESIA IRON FREE, PATCHOULI OIL INDONESIA MD, PATCHOULI OIL REDIST, PENNYROYAL HEART, PEPPERMINT ABSOLUTE MD, PETITGRAIN BIGARADE OIL TUNISIA, PETITGRAIN CITRONNIER OIL, PETITGRAIN OIL PARAGUAY TERPENELESS, PETITGRAIN OIL TERPENELESS STAB, PIMENTO BERRY OIL, PIMENTO LEAF OIL, RHODINOL EX GERANIUM CHINA, ROSE ABS BULGARIAN LOW METHYL EUGENOL, ROSE ABS MOROCCO LOW METHYL EUGENOL, ROSE ABS TURKISH LOW METHYL EUGENOL, ROSE ABSOLUTE, ROSE ABSOLUTE BULGARIAN, ROSE ABSOLUTE DAMASCENA, ROSE ABSOLUTE MD, ROSE ABSOLUTE MOROCCO, ROSE ABSOLUTE TURKISH, ROSE OIL BULGARIAN, ROSE OIL DAMASCENA LOW METHYL EUGENOL, ROSE OIL TURKISH, ROSEMARY OIL CAMPHOR ORGANIC, ROSEMARY OIL TUNISIA, SANDALWOOD OIL INDIA, SANDALWOOD OIL INDIA RECTIFIED, SANTALOL, SCHINUS MOLLE OIL, ST JOHN BREAD TINCTURE 10 PCT, STYRAX RESINOID, STYRAX RESINOID, TAGETE OIL, TEA TREE HEART, TONKA BEAN ABS 50 PCf SOLVENTS, TONKA BEAN ABSOLUTE, TUBEROSE ABSOLUTE INDIA, VETIVER HEART EXTRA, VETIVER OIL HAITI, VETIVER OIL HAITI MD, VETIVER OIL JAVA, VETIVER OIL JAVA MD, VIOLET LEAF ABSOLUTE EGYPT, VIOLET LEAF ABSOLUTE EGYPT DECOL, VIOLET LEAF ABSOLUTE FRENCH, VIOLET LEAF ABSOLUTE MD 50 PCT BB, WORMWOOD OIL TERPENELESS, YLANG EXTRA OIL, YLANG III OIL and combinations of these.

The colorants can be among those listed in the Color Index International by the Society of Dyers and Colourists. Colorants include dyes and pigments and include those commonly used for coloring textiles, paints, inks and inkjet inks. Some colorants that can be utilized include carotenoids, arylide yellows, diarylide yellows, β-naphthols, naphthols, benzimidazolones, disazo condensation pigments, pyrazolones, nickel azo yellow, phthalocyanines, quinacridones, perylenes and perinones, isoindolinone and isoindoline pigments, triarylcarbonium pigments, diketopyrrolopyrrole pigments, thioindigoids. Cartenoids include, for example, alpha-carotene, beta-carotene, gamma-carotene, lycopene, lutein and astaxanthin, Annatto extract, Dehydrated beets (beet powder), Canthaxanthin, Caramel, i-Apo-8'-carotenal, Cochineal extract, Carmine, Sodium copper chlorophyllin, Toasted partially defatted cooked cottonseed flour, Ferrous gluconate, Ferrous lactate, Grape color extract, Grape skin extract (enocianina), Carrot oil, Paprika, Paprika oleoresin, Mica-based pearlescent pigments, Riboflavin, Saffron, Titanium dioxide, Tomato lycopene extract; tomato lycopene concentrate, Turmeric, Turmeric oleoresin, FD&C Blue No. 1, FD&C Blue No. 2, FD&C Green No. 3, Orange B, Citrus Red No. 2, FD&C Red No. 3, FD&C Red No. 40, FD&C Yellow No. 5, FD&C Yellow No. 6, Alumina (dried aluminum hydroxide), Calcium carbonate, Potassium sodium copper chlorophyllin (chlorophyllin-copper complex), Dihydroxyacetone, Bismuth oxychloride, Ferric ammonium ferrocyanide, Ferric ferrocyanide, Chromium hydroxide green, Chromium oxide greens, Guanine, Pyrophyllite, Talc, Aluminum powder, Bronze powder, Copper powder, Zinc oxide, D&C Blue No. 4, D&C Green No. 5, D&C Green No. 6, D&C Green No. 8, D&C Orange No. 4, D&C Orange No. 5, D&C Orange No. 10, D&C Orange No. 11, FD&C Red No. 4, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, D&C Red No. 39, D&C Violet No. 2, D&C Yellow No. 7, Ext. D&C Yellow No. 7, D&C Yellow No. 8, D&C Yellow No. 10, D&C Yellow No. 11, D&C Black No. 2, D&C Black No. 3 (3), D&C Brown No. 1, Ext. D&C, Chromium-cobalt-aluminum oxide, Ferric ammonium citrate, Pyrogallol, Logwood extract, 1,4-Bis[(2-hydroxy-ethyl)amino]-9,10-anthracenedione bis(2-propenoic) ester copolymers, 1,4-Bis [(2-methylphenyl)amino]-9,10-anthracenedione, 1,4-Bis[4-(2-methacryloxyethyl) phenylamino] anthraquinone copolymers, Carbazole violet, Chlorophyllin-copper complex, Chromium-cobalt-aluminum oxide, C.I. Vat Orange 1, 2-[[2,5-Diethoxy-4-[(4-methylphenyl)thiol] phenyl]azo]-1,3,5-benzenetriol, 16,23-Dihydrodinaphtho [2,3-a:2',3'-i]naphth [2',3':6,7] indolo [2,3-c] carbazole-5,10,15,17,22,24-hexone, N,N'-(9,10-Dihydro-9,10-dioxo-1,5-anthracenediyl) bisbenzamide, 7,16-Dichloro-6,15-dihydro-5,9,14,18-anthrazinetetrone, 16,17-Dimethoxydinaphtho (1,2,3-cd:3',2',1'-lm) perylene-5,10-dione, Poly(hydroxyethyl methacrylate)-dye copolymers(3), Reactive Black 5, Reactive Blue 21, Reactive Orange 78, Reactive Yellow 15, Reactive Blue No. 19, Reactive Blue No. 4, C.I. Reactive Red 11, C.I. Reactive Yellow 86, C.I. Reactive Blue 163, C.I. Reactive Red 180, 4-[(2,4-dimethylphenyl) azo]-2,4-dihydro-5-methyl-2-phenyl-3H-pyrazol-3-one (solvent Yellow 18), 6-Ethoxy-2-(6-ethoxy-3-oxobenzo[b] thien-2(3H)-ylidene) benzo[b]thiophen-3(2H)-one, Phthalocyanine green, Vinyl alcohol/methyl methacrylate-dye reaction products, C.I. Reactive Red 180, C.I. Reactive Black 5, C.I. Reactive Orange 78, C.I. Reactive Yellow 15, C.I. Reactive Blue 21, Disodium 1-amino-4-[[4-[(2-bromo-1-oxoallyl)amino]-2-sulphonatophenyl]amino]-9,10-dihydro-9,10-dioxoanthracene-2-sulphonate (Reactive Blue 69), D&C Blue No. 9, [Phthalocyaninato(2-)] copper and mixtures of these.

Other than in the examples herein, or unless otherwise expressly specified, all of the numerical ranges, amounts, values and percentages, such as those for amounts of materials, elemental contents, times and temperatures of reaction, ratios of amounts, and others, in the following portion of the specification and attached claims may be read as if prefaced by the word "about" even though the term "about" may not expressly appear with the value, amount, or range. Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains error necessarily resulting from the standard deviation found in its underlying respective testing measurements. Furthermore, when numerical ranges are set forth herein, these ranges are inclusive of the recited range end points (e.g., end points may be used). When percentages by weight are used herein, the numerical values reported are relative to the total weight.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10. The terms "one," "a," or "an" as used herein are intended to include "at least one" or "one or more," unless otherwise indicated.

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While this invention has been particularly shown and described with references to preferred embodiments thereof, it will be understood by those skilled in the art that various changes in form and details may be made therein without departing from the scope of the invention encompassed by the appended claims.

What is claimed is:

1. A treatment facility comprising:
  a vault, having walls, ceiling, and a foundation; and
  within the vault, a material conveying system configured to convey biomass under an electron beam, wherein each of the walls comprises a plurality of discrete concrete units.

2. The facility as in claim 1, wherein the ceiling comprises a plurality of discrete units.

3. The facility as in claim 1, wherein the foundation comprises a concrete slab.

4. The facility as in claim 1, wherein the vault is re-configurable.

5. The facility as in claim 1, further comprising an electron irradiation device supported by the ceiling of the vault and disposed to irradiate biomass conveyed by the conveying system.

6. The facility as in claim 5, wherein the irradiation device weighs between about 5 and about 20 tons.

7. The facility as in claim 1, wherein each concrete unit has a volume of between about 6 ft$^3$ and 200 ft$^3$.

8. The facility as in claim 1, wherein the walls comprise interlocking concrete blocks.

9. The facility as in claim 1, wherein the concrete is selected from the group consisting of regular concrete, high density concrete, pre-tensioned concrete, lead containing concrete, rebar containing concrete and combinations thereof.

10. The facility as in claim 1, wherein the ceiling comprises a plurality of discrete concrete units.

11. The facility as in claim 10, wherein the concrete is selected from the group consisting of regular concrete, high density concrete, pre-tensioned concrete, lead containing concrete, rebar containing concrete and combinations thereof.

12. The facility as in claim 1, wherein the walls, ceiling and foundation are at least about 4 feet thick.

13. The facility as in claim 1, wherein the vault further comprises a substantially radiation opaque door.

14. The facility as in claim 1, further comprising an opening for continuously supplying biomass into the vault and to the conveying system, and openings for a continuous loop conveyor for continuously removing biomass from the conveying system and out of the vault.

15. The facility as in claim 14, wherein the conveying system comprises a vibratory conveyor.

16. The facility as in claim 1, wherein the conveying system comprises a first conveyor and a second conveyor, which the first conveyor is generally perpendicular to the second conveyor.

17. The facility as in claim 16, wherein the first conveyor comprises a cross-cut outlet for depositing biomass onto the second conveyor.

18. A method of treating a biomass material, the method comprising;
  irradiating a lignocellulosic biomass with an electron beam, in a vault having a foundation, walls and a ceiling,
  wherein each of the walls comprise a plurality of discrete concrete units.

19. The method of claim 18, wherein the ceiling comprises a plurality of discrete units.

20. The method of claim 18, wherein the walls comprise interlocking concrete blocks.

21. The method of claim 18, wherein the walls, ceiling and foundation include concrete and the concrete is selected from the group consisting of regular concrete, high density concrete, pre-tensioned concrete, lead containing concrete, rebar containing concrete and combinations thereof.

22. The method of claim 18, wherein the vault is re-configurable, and the method comprises re-configuring the vault after irradiating the biomass and irradiating a second biomass in the re-configured vault.

23. The method of claim 18, wherein the lignocellulosic material is in the form of a lumber product.

24. The method of claim 18, wherein the lignocellulosic material is selected from the group consisting of wood, particle board, sawdust, agricultural waste, sewage, silage, grasses, rice hulls, bagasse, cotton, jute, hemp, flax, bamboo, sisal, abaca, straw, corn cobs, corn stover, switchgrass, alfalfa, hay, coconut hair, seaweed, algae and mixtures thereof.

25. The method of claim 18, wherein irradiating the lignocellulosic biomass comprises irradiating the biomass on a conveyor.

26. The method of claim 25, wherein the conveyor comprises a vibratory conveyor.

* * * * *